(12) United States Patent
Swihart et al.

(10) Patent No.: US 9,933,565 B2
(45) Date of Patent: Apr. 3, 2018

(54) CONTACT IMAGING DEVICES FOR FLUORESCENCE APPLICATIONS

(71) Applicant: Bio-Rad Laboratories, Inc., Hercules, CA (US)

(72) Inventors: Steve Swihart, Walnut Creek, CA (US); Evan Thrush, San Anselmo, CA (US); Yochanan Uri, Givat Ela (IL); Boaz Ran, Kidron (IL); Itay Barak, Haifa (IT); Kevin McDonald, Novato, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/211,728

(22) Filed: Jul. 15, 2016

(65) Prior Publication Data
US 2017/0016829 A1    Jan. 19, 2017

Related U.S. Application Data

(60) Provisional application No. 62/193,833, filed on Jul. 17, 2015.

(51) Int. Cl.
*G02B 6/08* (2006.01)
*G02B 5/22* (2006.01)
*G01N 21/64* (2006.01)
*G02B 5/28* (2006.01)
*G01N 27/447* (2006.01)

(52) U.S. Cl.
CPC .......... *G02B 6/08* (2013.01); *G01N 21/6454* (2013.01); *G01N 27/44721* (2013.01); *G01N 2021/6484* (2013.01); *G02B 5/22* (2013.01); *G02B 5/28* (2013.01)

(58) Field of Classification Search
CPC ....................................................... G02B 6/08
See application file for complete search history.

(56) References Cited

U.S. PATENT DOCUMENTS

| | | | | |
|---|---|---|---|---|
| 4,922,092 A | * | 5/1990 | Rushbrooke | G01N 21/76 250/214 VT |
| 6,791,687 B1 | | 9/2004 | Rushbrooke et al. | |
| 7,612,342 B1 | | 11/2009 | Nagarkar | |

(Continued)

FOREIGN PATENT DOCUMENTS

WO    2014/062885 A1    4/2014

OTHER PUBLICATIONS

International Search Report and Written Opinion dated Oct. 4, 2016 in PCT/US16/42658, 10 pages.

*Primary Examiner* — David Porta
*Assistant Examiner* — Hugh H Maupin
(74) *Attorney, Agent, or Firm* — Kilpatrick Townsend & Stockton LLP

(57) ABSTRACT

Devices, systems, methods, and kits for contact imaging are provided. A contact imaging device includes an imaging sensor, a fixed fiber faceplate mechanically coupled to the imaging sensor, and an optical filtering layer mechanically coupled to the fixed fiber faceplate. The optical filtering layer can include an interference filter, an absorptive filter, and/or a removable fiber faceplate. The contact imaging device can be used to image fluorescent samples by filtering out excitation light on the basis of wavelength and/or angle of incidence.

22 Claims, 8 Drawing Sheets

(56) References Cited

U.S. PATENT DOCUMENTS

| | | | |
|---|---|---|---|
| 8,238,026 B1 * | 8/2012 | Kemme | G01J 4/04 |
| | | | 250/225 |
| 8,379,201 B2 | 2/2013 | Bielawksi | |
| 2002/0163641 A1 | 11/2002 | Shroder | |
| 2004/0109653 A1 * | 6/2004 | Kerr | G02B 6/08 |
| | | | 385/120 |
| 2007/0284250 A1 * | 12/2007 | Magnant | G01N 27/44739 |
| | | | 204/459 |
| 2009/0239759 A1 * | 9/2009 | Balch | B01J 19/0046 |
| | | | 506/9 |
| 2010/0148083 A1 * | 6/2010 | Brown | G01J 3/02 |
| | | | 250/372 |
| 2013/0092821 A1 | 4/2013 | Ozcan et al. | |
| 2013/0225441 A1 * | 8/2013 | Hassibi | C40B 30/04 |
| | | | 506/9 |
| 2014/0073043 A1 * | 3/2014 | Holmes | G01N 35/00 |
| | | | 435/287.3 |
| 2016/0247010 A1 * | 8/2016 | Huang | G02B 5/20 |

* cited by examiner

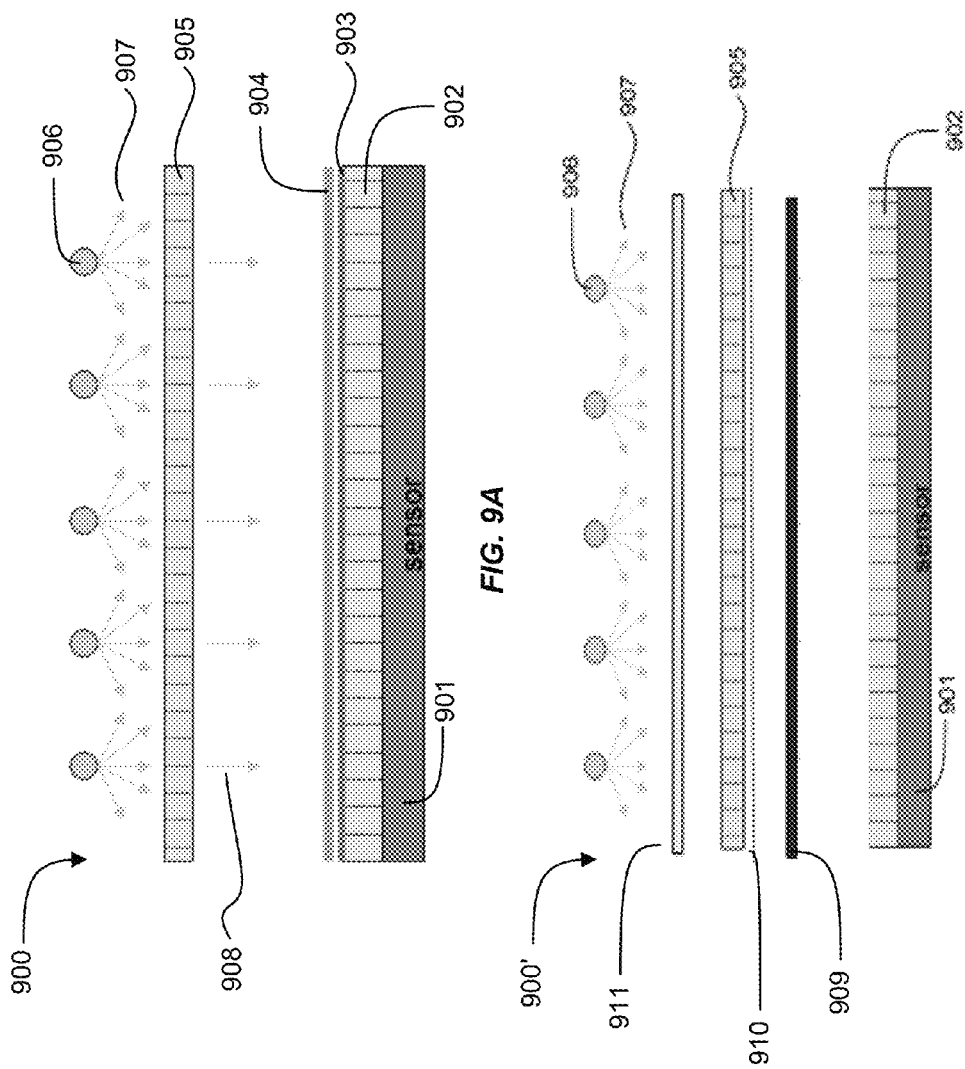

CONTACT IMAGING DEVICES FOR FLUORESCENCE APPLICATIONS

CROSS-REFERENCES TO RELATED APPLICATIONS

The present patent application is a non-provisional patent application claiming benefit of priority to U.S. Provisional Application No. 62/193,833, entitled "CONTACT IMAGING DEVICES FOR FLUORESCENCE APPLICATIONS", filed on Jul. 17, 2015, which is incorporated by reference herein for all purposes. The present application is also related to U.S. patent application Ser. No. 14/789,717, entitled "CONTACT IMAGER", and filed Jul. 1, 2015, the entire disclosure of which is incorporated by reference herein for all purposes.

BACKGROUND OF THE INVENTION

Many procedures that are performed in biochemical laboratories involve analyses of multiple samples or materials distributed over a two-dimensional area. Examples of such procedures are screening studies performed on substances that are placed in individual wells of a multi-well plate such as a standard 96-well microtiter plate or larger plates, or on molecular species that are applied as droplets or regularly spaced spots, either microscopic in size or larger, on a solid surface. Further examples are slab-shaped electrophoresis gels in which either two-dimensional electrophoretic separations or one-dimensional separations of multiple samples in parallel have been performed. Still further examples are blotting membranes to which electrophoretically separated species in the form of spots or bands have been transferred from a slab gel. Other examples will readily occur to the skilled biochemist.

In all of these examples, detection and analysis of individual sites in the two-dimensional array can make use of radiation associated with each site. Detection can simply determine the presence or absence of particular species, or can also include quantitative determinations, either on an absolute basis or as comparisons among different sites. In some cases, the detected radiation results from the decay of radionuclides. In other cases, the detected radiation is light, which can be transmitted, absorbed, or reflected by each site, or generated by the materials at the sites themselves. Species in electrophoresis gels or blotting membranes, for example, are commonly detected by fluorescence, chemiluminescence, or bioluminescence, either as inherent characteristics of the species at the sites or as a result of treatment of the species once they are separated throughout the two-dimensional array. The treatment may include binding reactions in which energy-emitting labels are attached to the species, or irradiation of the species or the labels with excitation energy that will cause them to emit light energy, most often at different wavelengths.

In contact imaging, a two-dimensional array as discussed above is placed in close proximity to a sensor, and radiation originating from species in the array is imaged using the sensor. Examples of suitable sensors include conventional photographic film, amorphous silicon (a-Si) sensors, as well as charge-coupled devices (CCDs) and complementary metal-oxide-semiconductor (CMOS) devices. A sensor can be constructed to be planar or two-dimensional in shape, and have dimensions similar to those of the arrays it is used to image. Due to the short distance and large area of exposure between the array and sensor, contact imaging allows weak radiation sources to be detected at high spatial resolution.

Many applications of contact imaging have been optimized for radiation sources that do not require energy to be input at the time of detection. For example, conventional cassettes that hold sample arrays against photographic film are often impervious to outside light, and require that arrays contain endogenous (e.g., chemiluminescent) light sources. Such cassettes are not suitable for imaging fluorescent samples, which generally emit long-wavelength light in response to excitation with short-wavelength light. Because most fluorophores have excited-state lifetimes on the order of nanoseconds, it is impractical to excite fluorophores in an array and then enclose the array in a dark container for contact imaging.

Adapting contact imaging devices and procedures for fluorescent species presents technical challenges. The sample array must be exposed to excitation light at the time of imaging, but an image of species in the array must be formed mainly from fluorescently emitted light rather than excitation light. Contact between the array and sensor limits options for preventing excitation light from reaching the sensor.

BRIEF SUMMARY OF THE INVENTION

Provided herein are devices, systems, methods, and kits for contact imaging.

In a first aspect of the present invention, a contact imaging device is provided. The contact imaging device comprises an imaging sensor, a fixed fiber faceplate mechanically coupled to the imaging sensor, and an optical filtering layer mechanically coupled to the fixed fiber faceplate. In some embodiments, the fixed fiber faceplate has a numerical aperture of at most about 0.1, 0.2, 0.3, 0.4, 0.5, 0.6, 0.7, 0.8, 0.9, 1.0, or at increments or gradients within the range of about 0.1 to 1.0.

In some embodiments of the contact imaging device, the optical filtering layer comprises an interference filter. The interference filter can be a long-pass filter, can block ultraviolet light, and/or can pass visible light. For example, the interference filter can pass light having wavelengths in the range 400-550, 400-500, 400-450, 400-425, 425-450, 450-475, 475-500, 500-525, or 525-550 nm. In these embodiments, in addition to the interference filter, the optical filtering layer can further comprise an absorptive filter. The absorptive filter can comprise colored glass, and/or be disposed between the interference filter and the fixed fiber faceplate.

In some embodiments, the optical filtering layer of the contact imaging device comprises an absorptive filter. The absorptive filter can comprise colored glass. In these embodiments, the fixed fiber faceplate can have a numerical aperture of at most about 0.1, 0.2, 0.3, 0.4, 0.5, 0.6, 0.7, 0.8, 0.9, 1.0, or at increments or gradients within the range of about 0.1 to 1.0, for example. Instead or in addition, the fixed fiber faceplate can comprise a plurality of optical fibers, and the core or the cladding of at least one of the optical fibers can comprise an absorptive material.

In some embodiments of the contact imaging device, the optical filtering layer comprises a removable fiber faceplate and an optical filter, the removable fiber faceplate is coated on one side with the optical filter, and the optical filtering layer is configured to be removed from the fixed fiber faceplate. The transmission filter can be an interference filter or an absorptive filter, for example. The numerical aperture of the removable fiber faceplate can be at most about 0.1, 0.2, 0.3, 0.4, 0.5, 0.6, 0.7, 0.8, 0.9, or 1.0, for example, and/or can be less than that of the fixed fiber faceplate (for example, by at least about 0.01, 0.02, 0.05, 0.1, 0.2, 0.3, 0.4, 0.5, 0.6, 0.7, 0.8, 0.9, 0.95, or 0.99). The removable fiber faceplate can be disposed between the fixed fiber faceplate and the optical filter.

In some embodiments, the transmission filter is disposed between the fixed fiber faceplate and the removable fiber faceplate. In these embodiments, the transmission filter can be in contact with the fixed fiber faceplate, and/or be an interference filter. The removable fiber faceplate can have a numerical aperture of at most about 0.1, 0.2, 0.3, 0.4, 0.5, 0.6, 0.7, 0.8, 0.9, or 1.0, for example, and/or the fixed fiber faceplate can have a numerical aperture of at least about 0.1, 0.2, 0.3, 0.4, 0.5, 0.6, 0.7, 0.8, 0.9, 0.95 or 0.99, for example.

In some embodiments of the contact imaging device, the fixed fiber faceplate is a fiber optic taper. In some embodiments, the fixed fiber faceplate comprises a plurality of optical fibers, and the core or the cladding of at least one of the optical fibers comprises an absorptive material. For example, the core of at least one optical fiber, the cladding of at least one optical fiber, and/or the core or the cladding of all of the optical fibers can comprise an absorptive material.

In some embodiments, the angle of acceptance of optical fibers of the fixed fiber faceplate is at most about 1, 2, 3, 4, 5, 6, 7, 8, 9, 10, 20, 30, 40, 50, 60, 70, 80, or 90 degrees, for example. In some embodiments, the fixed fiber faceplate comprises a plurality of black fibers interspersed among a plurality of optical fibers. The black fibers can have circular or hexagonal cross-sections, and/or be disposed in interstitial spaces between the optical fibers. The ratio of the number of black fibers to the number of optical fibers in the fixed fiber faceplate can be at most about 1:1,000, 1:500, 1:200, 1:100, 1:50, 1:20, 1:10, 1:5, 1:2, 1:1, 2:1, 5:1, 10:1, 20:1, 50:1, 100:1, 200:1, 500:1, or 1,000:1 (for example), and/or the black fibers can occupy at most about 0.1, 0.2, 0.5, 1, 2, 5, 10, 20, 50, 90, 95, or 99 percent (for example) of the cross-sectional area of the fixed fiber faceplate.

In a second aspect of the present invention, a system for imaging a fluorescent, phosphorescent, or chemiluminescent sample is provided. The system comprises an excitation light source and the contact imaging device described above. In some embodiments, the system further comprises a fluorescent, phosphorescent, or chemiluminescent sample. In some embodiments, the system further comprises a cassette, wherein the cassette comprises a base plate and a light-tight lid, and the contact imaging device is mechanically coupled to the base plate. The base plate can comprise a thermally conductive metal slab, and the imaging sensor can be coupled to the metal slab. In some embodiments, the system further comprises an excitation fiber faceplate, wherein the excitation fiber faceplate is configured to be disposed between the excitation light source and the sample. The excitation fiber faceplate can be mechanically coupled to the excitation light source. The excitation fiber faceplate can have a numerical aperture of at most about 0.1, 0.2, 0.3, 0.4, 0.5, 0.6, 0.7, 0.8, 0.9, or 1.0, for example. Light emitted by the excitation light source and transmitted by the excitation fiber faceplate can be collimated.

In some embodiments of the system, the excitation light source emits collimated light. In some embodiments, the excitation light source is positioned relative to the contact imaging device such that light emitted by the excitation light source is not incident on the optical filtering layer. In some embodiments, the excitation light source is positioned relative to the contact imaging device such that light emitted by the excitation light source is incident on the optical filtering layer at an angle of at least about 1, 2, 3, 4, 5, 6, 7, 8, 9, 10, 20, 30, 40, 50, 60, 70, 80, or 90 degrees (for example) from the normal. In some embodiments, the excitation light source is positioned relative to the contact imaging device such that the excitation light source emits light in a direction parallel to the surface of the optical filtering layer.

Any embodiment of the system can be configured such that light emitted by the excitation light sources passes through the sample.

In a third aspect of the present invention, a method for imaging a fluorescent, phosphorescent, or chemiluminescent sample is provided. The method comprises placing a sample in proximity to the contact imaging device described above, exposing the sample to an excitation light source, and obtaining an image of the sample using the imaging sensor of the contact imaging device.

In some embodiments of the method, exposing the sample and obtaining an image of the sample occur simultaneously. In some embodiments, the image of the sample is obtained using time-resolved fluorescence techniques. In some embodiments, prior to obtaining an image of the sample, the sample is exposed to the excitation light source and the excitation light source is then turned off. In some embodiments, the sample is phosphorescent. Some embodiments of the method further comprise applying an image sharpening algorithm to the image of the sample.

In a fourth aspect of the present invention, a kit is provided. The kit comprises an imaging sensor mechanically coupled to a fixed fiber faceplate, a first optical filtering layer, and a second optical filtering layer, wherein each optical filtering layer: comprises a removable fiber faceplate and an optical filter, the removable fiber faceplate being coated on one side with the optical filter; and is configured to be mechanically coupled to the fixed fiber faceplate.

In some embodiments of the kit, the transmission filter of the first optical filtering layer is an interference filter and the transmission filter of the second optical filtering layer is an absorptive filter. In some embodiments, the optical filters of the first and second optical filtering layers pass light in different wavelength bands. In some embodiments, the removable fiber faceplates of the first and second optical filtering layers have different numerical apertures. In some embodiments, the first optical filtering layer is configured for the removable fiber faceplate to be disposed between the fixed fiber faceplate and the optical filter, and the second optical filtering layer is configured for the transmission filter to be disposed between the fixed fiber faceplate and the removable fiber faceplate.

BRIEF DESCRIPTION OF THE DRAWINGS

Illustrative aspects and embodiments are described in detail below with reference to the following drawing figures.

FIG. 9A shows a system 900 for imaging a fluorescent sample according to some embodiments of the present invention. A contact imaging device includes imaging sensor 901, fixed fiber faceplate 902, and optical filtering layer 903. Optical filtering layer 903 includes an optical filter, such as an interference filter or an absorptive filter. Two-dimensional sample array 904 is placed in contact with optical filtering layer 903 and lies roughly flat. An excitation fiber faceplate 905 is disposed between excitation light source 906 and sample array 904. Thus, light 907 emitted by excitation light source 906 is collimated, and light rays 908 strike sample array 904 and optical filtering layer 903 at low or near-zero angles of incidence.

FIG. 9B shows a system 900' for imaging a fluorescent sample according to some embodiments of the present invention. A contact imaging device includes imaging sensor 901 and a fixed fiber faceplate 902. An excitation fiber faceplate 905 is disposed between excitation light source 906 and fixed fiber faceplate 902. An alternative optical filtering layer 910 includes an optical filter, such as an interference filter, a dielectric, or an absorptive filter, disposed on the excitation fiber faceplate 905 facing the fixed fiber faceplate 902. An absorbance glass 909 is placed in series with the fixed fiber faceplate 902. Thus, light 907 emitted by excitation light source 906 is collimated and at least in part filtered, and light rays strike fixed fiber faceplate 902 at low or near-zero angles of incidence. Also shown is the sample gel 911 (or sample blot) that is illuminated by the light source 906, in contact with excitation fiber faceplate 905 and which lies roughly flat.

DETAILED DESCRIPTION OF THE INVENTION

A. Introduction

Figure 1:
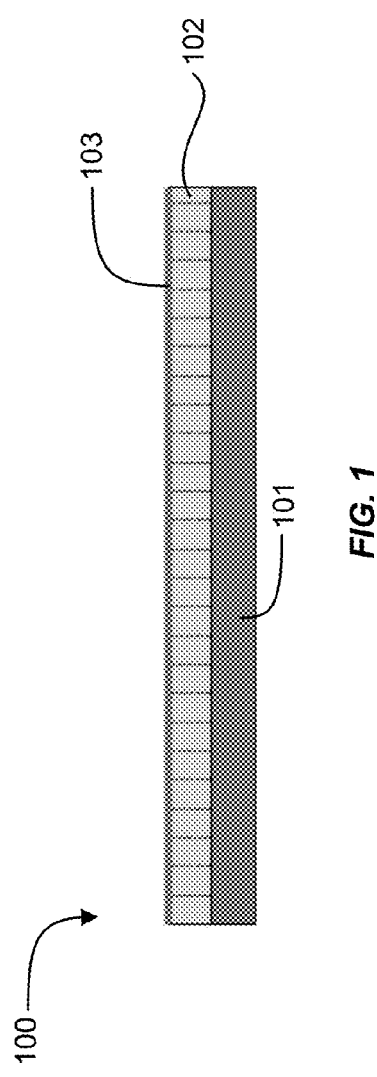
FIG. 1 shows a contact imaging device 100 according to some embodiments of the present invention. Imaging sensor 101 is mechanically coupled to fixed fiber faceplate 102, which is in turn mechanically coupled to interference filter 103.

The inventors have found that devices combining fiber faceplates and optical filters are suitable for the contact imaging of fluorescent species or samples. A device includes one or more fiber faceplates, and one or more optical filters, mechanically coupled to each other and placed on the sample side of an imaging sensor. Such a device can be configured to pass light fluorescently emitted by species in a sample while blocking excitation light. The devices can select light on the basis of wavelength, as well as the angle at which light approaches the sensor. Devices, systems, methods, and kits for performing contact imaging are provided herein.

B. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The following definitions are provided to facilitate understanding of certain terms used frequently herein and are not meant to limit the scope of the present disclosure.

The term "membrane" includes blots and membranes (e.g., nitrocellulose, nylon polyvinylidene fluoride (PVDF), and other materials commonly used in the art). A membrane can also be paper or a paper blend, e.g., where the assay involves transfer of a gel and drying on the paper. A "sample membrane" refers to a membrane carrying sample, e.g., transferred from a gel or applied directly.

"Analyte" refers to a molecule or molecular complex that can be detected or imaged as provided herein. Analytes can be biological in origin or can be synthetic. Analytes can include peptides, proteins, nucleic acids, carbohydrates, lipids, viruses, metabolites, hormones, cofactors, vitamins, drugs, and/or small molecules. Without limitation, analytes can be polar, charged, hydrophilic, hydrophobic, monomeric, oligomeric, or polymeric and can have any molecular weight.

The term "sample" or "biological sample" encompasses a variety of sample types obtained from an organism. The term encompasses bodily fluids such as blood, blood components, saliva, serum, plasma, urine and other liquid samples of biological origin, solid tissue biopsy, tissue cultures, or supernatant taken from cultured cells. A biological sample can be processed prior to assay, e.g., to remove cells or cellular debris. The term encompasses samples that have been manipulated after their procurement, such as by treatment with reagents, solubilization, sedimentation, or enrichment for certain components. A sample can contain analytes.

"Sample array" refers to a physical matrix in which analytes of one or more samples are separated and/or distributed. Some sample arrays are two-dimensional in that they contain analytes from one sample distributed over two or more dimensions, or contain analytes from multiple samples, where the analytes from each sample are distributed over one or more dimensions. Examples of sample arrays are multi-well plates, micro-titer plates, slab-shaped electrophoresis gels, and blotting membranes.

As used herein, an "immunoassay" refers to assays that rely on antibody-antigen interactions. Examples include Western blots (antigen transferred to membrane, membrane exposed to antibody, and in some embodiments, secondary antibody); ELISAs; and other affinity-based labeling assays.

The term "antibody" as used herein refers to a polypeptide that specifically binds and recognizes an analyte (antigen). The term encompasses antibodies encoded by an immunoglobulin gene or immunoglobulin genes, recombinant and/or clonal variants thereof, and fragments thereof. A full-length antibody is a tetramer. Each such tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively. The recognized immunoglobulin light chains are classified as either kappa or lambda. Immunoglobulin heavy chains are classified as gamma, mu, alpha, delta, or epsilon, which in turn define the immunoglobulin classes, IgG, IgM, IgA, IgD and IgE, respectively.

The terms "specific for," "specifically binds," and like terms refer to a molecule (e.g., antibody or antibody fragment) that binds to its target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a given antibody target will typically bind the antibody target with at least a 2-fold greater affinity than a non-antibody target. Specificity can be determined using standard methods, e.g., solid-phase ELISA immunoassays (see, e.g., Harlow & Lane, *Using Antibodies, A Laboratory Manual* (1998) for a description of immunoassay formats and conditions that can be used to determine specific immunoreactivity).

The term "binds," when used with respect to an antibody target (e.g., antigen, analyte), typically indicates that an antibody binds a majority of the antibody targets in a pure population (assuming appropriate molar ratios). For example, an antibody that binds a given antibody target typically binds to at least ⅔ of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

The terms "label," "detectable label," "detectable moiety," and like terms refer to a composition detectable by spectroscopic, photochemical, biochemical, immunochemical, chemical, or other physical means. In the context of the present disclosure, labels typically include luminescent agents, electron-dense reagents, enzymes (e.g., as commonly used in an ELISA), biotin, digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of dyes that provides a unique detectable signature, e.g., at a particular wavelength or combination of wavelengths. Any method known in the art for conjugating label to a desired agent may be employed, e.g., using methods described in Hermanson, *Bioconjugate Techniques* 1996, Academic Press, Inc., San Diego.

The term "positive," when referring to a result or signal, indicates the presence of an analyte or item that is being detected in a sample. The term "negative," when referring to a result or signal, indicates the absence of an analyte or item that is being detected in a sample. Positive and negative are typically determined by comparison to at least one control, e.g., a threshold level that is required for a sample to be determined positive, or a negative control (e.g., a known blank).

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters, and will understand which controls are valuable in a given situation and be able to analyze data based on comparisons to control values. Controls are also valuable for determining the significance of data. For example, if values for a given parameter are variable in controls, variation in test samples will not be considered as significant.

Two objects are "mechanically coupled," as the term is used herein, if they are in contact with each other, and the movement of one object with respect to the other is constrained or hindered, such as by friction. The amount of constraint or hindrance of movement can be engineered for a desired application of the two objects. For example, in a mechanical coupling between an imaging sensor and a fiber faceplate, the fiber faceplate can be held in place so that consistent images can be acquired over a desired period of time using light that passes through the faceplate and onto the sensor. Mechanically coupled objects can be separated using tools, force, or otherwise at an appropriate time.

The term "angle of incidence," in the context of a ray of light incident on a surface, has the conventional meaning, i.e., the angle between the ray of light and a line normal to the surface.

The term "angle of acceptance" has the conventional meaning, i.e., the maximum angle of incidence at which a ray of light can approach the end of an optical fiber and be transmitted through the optical fiber. When applied to a fiber faceplate, the term refers to the angle of acceptance for optical fibers making up the fiber faceplate.

The term "numerical aperture" (abbreviated as "NA") has the conventional meaning and is a dimensionless number characterizing the range of angles of incident light that an optic such as a lens or fiber optic can accept. In some cases, for fiber optics, NA=n sin($\theta$), as measured in air, where n is the index of refraction of the working medium and $\theta$ is the angle of acceptance.

The term "black" refers to materials that absorb substantially all wavelengths of visible light, so that these materials appear black. In some cases, black materials transmit and/or reflect substantially no visible light, or less (e.g., 1.5, 2, 5, 10, 20, 50, 100, 200, 500, 1000, 100,000, 1,000,000, or 10,000,000-fold) visible light than they absorb. Neutral-density filters, rated ND2, ND4, ND8, ND16, ND32, ND64, ND100, ND128, ND256, ND512, ND1000, ND1024 or greater, are examples of optics incorporating black materials.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

C. Sensors

Any convenient imaging sensors can be included in the present devices. Examples of suitable imaging sensors are complementary metal-oxide-semiconductor (CMOS) sensors or charge coupled device (CCD) sensors. Such sensors and methods of use are familiar in the art, e.g., Fraden (Springer, $4^{th}$ ed.) Handbook of Modern Sensors: Physics, Designs, and Applications; Cabello et al. (2007) *Phys Med Biol* 52:4993. Useful sensors are available from a number of commercial suppliers, e.g., Canon, Samsung, Toshiba, CMOS Sensor, etc. Instead or in addition, imaging sensors can include photographic film.

Both CCD and CMOS sensors have 2-D arrays of thousands or millions of tiny cells, each of which transforms the signal (light or radiation) from one small portion of the image into electrons. Once an image is captured on the sensor, the next step is to read the value (accumulated charge) of each cell in the image. In a CCD device, the charge is transported across the chip and read at one corner of the array. An analog-to-digital converter turns each pixel's value into a digital value. In most CMOS devices, there are several transistors at each pixel that amplify and move the charge using more traditional wires. The CMOS approach is more flexible because each pixel can be read individually. CCD sensors use a special manufacturing process allowing charge to be transported across the chip without distortion. This process leads to very high-quality sensors in terms of fidelity and light sensitivity.

Current CCD and CMOS imaging systems e.g., the C-DiGit Blot Scanner, Dexela, and myECL Imager systems, are limited to producing digital images. Similar imaging technology and software can be employed in the presently described devices and systems. The cassettes described below can be conveniently linked to a computer or scanner during or after exposure to detect the presence, absence, and/or strength of a signal.

A signal from the sensor can be acquired using a control board, which can be placed, for example, adjacent to the sensor in the device, or externally. The sensor can thus be connected to the board with a cable or via a port or wireless connection. The control board can then communicate with an external device providing a user interface. The external device can include a touch screen, processor, or storage device. Examples of external devices include hand-held devices (e.g. smartphones or tablets), laptop computers, and desktop computers. The external device can be accessed by cables or ports (e.g., USB or Ethernet) on a cassette enclosing the contact imaging device or by wireless signals (e.g., WiFi or Bluetooth).

In some embodiments, the imaging sensor or entire contact imaging device can be cooled during exposure. Cooler temperatures reduce dark current (a potential source of noise) in digital sensors, and enable longer exposure times, which can increase sensitivity. Cooling does, however, slow chemical reactions (e.g., chemiluminescence or fluorescence) that can give rise to optical signals. The user can determine whether to cool the imaging sensor based on speed and sensitivity considerations.

D. Devices

A contact imaging device according to embodiments of the present invention includes an imaging sensor, as disclosed above, and a fixed fiber faceplate mechanically coupled to the imaging sensor. A fiber faceplate (also called a fiber optic faceplate, a fiber optic plate (FOP), a fiber plate, or simply a faceplate) is a coherent bundle of short optical fibers. Where a fiber faceplate has a plurality of coherent bundles of short optical fibers, and the fiber faceplate is optically coupled to a sensor, it is desirable to provide for a sufficient density of fibers per coherent bundle such that fibers from one coherent bundle focused on a desired sensor element and do not optically "bleed over" or create visual noise in adjacent or proximate sensor elements of a sensor. In some aspects, The fixed fiber faceplate can include, for example, at least about 2, 5, 10, 20, 50, 100, 200, 500, or 1,000, 2,000, 5,000, or 10,000 optical fibers, which are also called 'constituent fibers' herein. In other aspects, the number of constituent fibers can be determined according to density per sensor element, or sensor pixel. In such aspects, the ratio of consistent fibers per sensor pixel can be 2:1, 5:1, 10:1, 15:1, 20:1, 80:1, 100:1, 200:1, 500:1, 1,000:1, 10,000:1, or at ratio increments within this range. In some implementations, a sensor pixel can be from about five micrometers to about two hundred micrometers (5 µm-200 µm) in a surface dimension (e.g. width, diameter), or at increments or gradients thereof. In specific implementations, a sensor pixel can be about eighty micrometers (80 µm) or about one hundred fifty micrometers (150 µm).

Each optical fiber includes a core and cladding, and can transmit light along its length, from one side of the fiber faceplate to another side, through total internal reflection. In some embodiments, the optical fibers are parallel to each other. Fiber faceplates are commercially available from InCom, Inc. (Charlton, Mass., USA), ProxiVision GmbH (Bensheim, Germany), Collimated Holes, Inc. (Campbell, Calif., USA), Fiberoptic Systems, Inc. (Simi Valley, Calif., USA), Edmund Optics (Barrington, N.J., USA), and others. Fiber faceplates can be prepared from glass (e.g., low melting point glasses, such as borosilicates, and lead-based glasses), or from organic polymers such as polycarbonate and polystyrene.

In some embodiments, the fiber faceplate is planar on one or both surfaces where the constituent fibers terminate, and has a flat shape overall. Thus, the fiber faceplate can directly adjoin a planar imaging sensor, and can separate the sensor from a two-dimensional sample array (e.g., an electrophoresis gel or blotting membrane) while conforming to the shape of the sample array. In some embodiments, the fiber faceplate is positioned so that the constituent optical fibers are oriented perpendicular to the imaging sensor and/or the sample array. In some embodiments, the fiber faceplate is coupled to the sensor such that the constituent optical fibers are specifically aligned with pixels of the sensor. For example, each optical fiber can terminate at one or more pixels, or each pixel can span the cross-section(s) of one or more optical fibers. Any available mechanism can be used to couple the fiber faceplate to the imaging sensor. For example, they can be coupled together using screws or transparent glue. In embodiments where the imaging sensor is photographic film, the film can be inserted in a frame that is in turn coupled to the fiber faceplate, so that a new piece of film can be used for each exposure. If desired, a protective or non-reflective coating can be applied to one or more surfaces of the fiber faceplate.

Transmission of light through a fiber faceplate can preserve an image from one surface of the fiber faceplate to the next. Thus, when the transmitted light is used to form an image, a thicker fiber faceplate can be used in lieu of glass or plastic to obtain an image of comparable quality. The fixed fiber faceplate used in some embodiments of the present contact imaging devices has a thickness of at least about 0.1, 0.2, 0.5, 1, 2, 5, 10, 20, or 50 mm, or increments and gradients thereof. A thicker fiber faceplate can provide more mechanical support to the imaging sensor to which it is coupled, and/or to the two-dimensional sample array being imaged. Further, the thickness of the fixed fiber faceplate can provide for a thermal resistor for maintaining a temperature. In further implementations, the fixed fiber faceplate can have a tapered structure, in part focusing or concentrating the path of light, where the fixed fiber faceplate can have a thickness 10, 20, 50, or 100 mm, or increments and gradients thereof.

Some embodiments of the contact imaging devices include fixed fiber faceplates engineered to admit light at low angles of incidence. In these embodiments, the faceplate can transmit (i.e., accept) light that approaches at an angle roughly perpendicular to the faceplate surface, and absorb, reflect, or otherwise block (i.e., reject) light that approaches at higher angles of incidence, for example roughly parallel to the faceplate surface. Instead or equivalently, light that approaches the constituent fibers of the faceplate roughly parallel to the long axes of these fibers (i.e., at a small angle of incidence) can be accepted, while light roughly perpendicular to the fiber axes (i.e., at a large angle of incidence) can be rejected. In some embodiments, the fixed fiber faceplate has a low numerical aperture, for example at most about 0.1, 0.2, 0.3, 0.4, 0.5, 0.6, 0.7, 0.8, 0.9, or 1.0. In some embodiments, the angle of acceptance of optical fibers of the fixed fiber faceplate is at most about 1, 2, 3, 4, 5, 6, 7, 8, 9, 10, 20, 30, 40, 50, 60, 70, 80, or 90 degrees. A fiber faceplate having a low numerical aperture and/or angle of acceptance can be useful for discriminating between light fluorescently emitted from species in the sample array on the one hand, and excitation light originating from outside the sample array on the other hand. For example, the faceplate can accept and transmit light passing directly from the sample array to the imaging sensor, and reject (block) light from the periphery of the sample array. A low numerical aperture and/or angle of acceptance can also increase the depth of field of the fiber faceplate, which can be useful for imaging thick sample arrays, or sample arrays separated from the fiber faceplate and imaging sensor by one or more intervening layers of material.

The contact imaging device also includes an optical filtering layer mechanically coupled to the fixed fiber faceplate. The optical filtering layer can filter light on the basis of wavelength, by passing wavelengths of light of interest and blocking other wavelengths. Any type of filter can be used in the optical filtering layer, such as an absorptive filter, interference filter, dichroic filter, long-pass filter, short-pass filter, band-pass filter, band-rejection filter, multi-band filter, broadband filter, or neutral-density filter. The optical filtering layer can be mechanically coupled to the fixed fiber faceplate as desired, for example using adhesives or fasteners.

In some embodiments, the optical filtering layer is positioned on the opposite side of the fixed fiber faceplate from the imaging sensor, such that the optical filtering layer, fixed fiber faceplate, and imaging sensor are stacked one on top of the other. Thus, the fixed fiber faceplate can be sandwiched between the imaging sensor and optical filtering layer, and receive light that has been filtered through the optical filtering layer. Like the imaging sensor and fixed fiber faceplate, the optical filtering layer can be flat, planar, and/or complementary in shape to the sample array. The optical filtering layer can be configured to directly contact the sample array.

In some embodiments, the optical filtering layer includes an interference filter (FIG. 1). Interference filters generally include multiple layers of glass, plastic, or other dielectric materials having different refractive indices. At interfaces between these layers, light can be transmitted or reflected, depending on the angle of incidence, wavelength, and other factors. Interference filters, also sometimes referred to as dichroic filters or thin-film filters, are commercially available from Edmund Optics (Barrington, N.J., USA) and Omega Optical (Brattleboro, Vt., USA), among others. In some embodiments, the interference filter is a long-pass filter, for example passing wavelengths of light greater than 400, 450, 500, 550, 600, 650, 700, 750, 800, or 850 nm, or increments, ranges, and gradients thereof. In some embodiments, the interference filter blocks ultraviolet light and/or passes visible light. The interference filter can be configured to pass wavelengths of light emitted by commonly used chemiluminescent substrates or fluorophores. For example, the filter can pass light having wavelengths in the range of about 400-550, 400-500, 400-450, 400-425, 425-450, 450-475, 475-500, 500-525, or 525-550 nm. The interference filter also can be configured to block wavelengths of light commonly used to excite fluorophores, for example wavelengths in the near-ultraviolet range, light having a wavelength of from about 350 to 400 nm, or light emitted from a chemiluminescent source.

Instead of or in addition to an interference filter, the optical filtering layer can include an absorptive filter. Absorptive filters absorb certain wavelengths of light and transmit other wavelengths. Some absorptive filters contain organic dyes or pigments, or other colored organic or inorganic materials. Examples of absorptive filters include colored glass filters and plastic (e.g., polycarbonate or acrylic) filters. Absorptive filters are available from Newport Corporation (Irvine, Calif., USA), Thorlabs, Inc. (Newton, N.J., USA), and Schott AG (Mainz, Germany), as well as from other sources.

Figure 2:
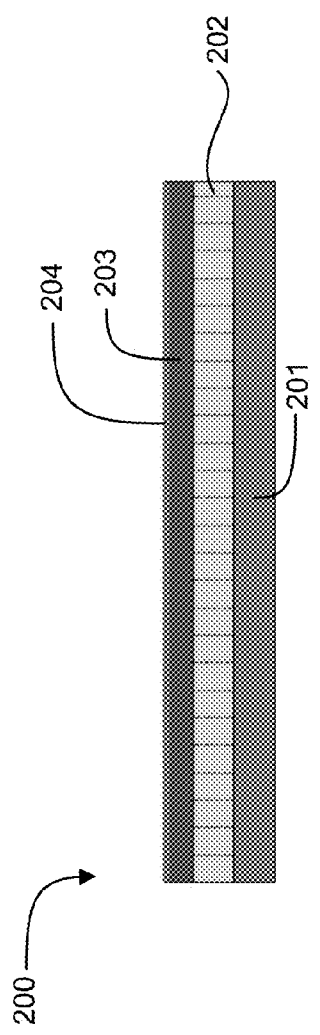
FIG. 2 shows a contact imaging device 200 according to some embodiments of the present invention. Imaging sensor 201 is mechanically coupled to fixed fiber faceplate 202, which is in turn mechanically coupled to an optical filtering layer. The optical filtering layer includes absorptive filter 203 and interference filter 204. The interference filter is placed on the opposite side of the absorptive filter from the fixed fiber faceplate and imaging sensor.

Absorptive filters generally transmit progressively less light as the angle of incidence is increased, whereas interference filters transmit more light. Therefore, to control the angles and wavelengths of light passed to the fixed fiber faceplate and imaging sensor in the present devices, absorptive and interference filters can be substituted for each other or used in combination. In some embodiments, the optical filtering layer includes both an absorptive and an interference filter. For example, the interference filter can be placed in front of the absorptive filter relative to the fixed fiber faceplate and imaging sensor, so that the absorptive filter is disposed between the interference filter and the fixed fiber faceplate (FIG. 2). Thus, light from the sample array passes first through the interference filter and then through the absorptive filter. In this configuration, light of undesired wavelengths can be filtered out in steps, with such light at low angles of incidence being filtered out by the interference filter and light at high angles of incidence filtered out by the absorptive filter. Alternatively, filtering can occur in the opposite order, with the interference filter disposed between the absorptive filter and the fixed fiber faceplate. Various configurations of an interference filter and an absorptive filter in the optical filtering layer will be apparent to the skilled artisan.

For flexibility in imaging various kinds of sample arrays and the species they contain, the optical filtering layer can be removable. For example, the optical filtering layer can be configured to mechanically attach to the fixed fiber faceplate and later detach at an appropriate time. Reversible mechanisms can be used for attachment and detachment, such as screws, rails, or clamps. In some embodiments (discussed below), the contact imaging device is provided as a kit with two or more optical filtering layers, each with a different configuration of optical components. Any one of these layers can be coupled to the fixed fiber faceplate, and the optical filtering layers collectively can be used for different wavelength ranges (e.g., for excitation of species in the sample array or emission by these species), different sample array characteristics (e.g., thickness or composition), and other variable conditions for imaging.

Figure 3:
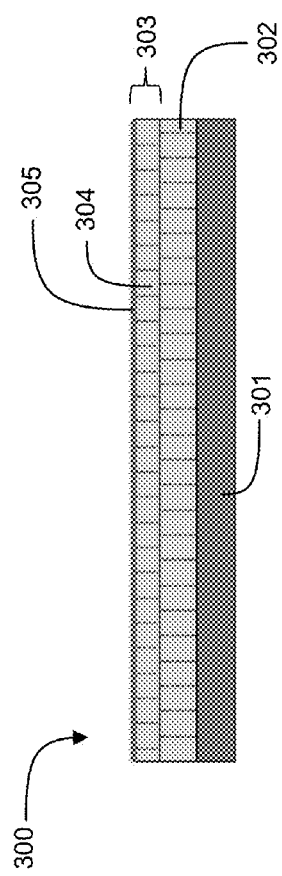
FIG. 3 shows a contact imaging device 300 according to some embodiments of the present invention. Imaging sensor 301 is mechanically coupled to fixed fiber faceplate 302, which is in turn mechanically coupled to optical filtering layer 303. The optical filtering layer includes removable fiber faceplate 304, and transmission filter 305 coated on one side of the removable fiber faceplate. The removable and fixed fiber faceplates are stacked one on top of the other, so that light transmitted by transmission filter 305 can be guided to imaging sensor 301.

In some embodiments, the optical filtering layer contains a removable fiber faceplate as well as an transmission filter (e.g., an interference filter or an absorptive filter). The removable fiber faceplate is similar to the fixed fiber faceplate and comprises a coherent bundle of short optical fibers. Due to the light-guiding nature of fiber faceplates, two or more fiber faceplates can be stacked together, and an image can be formed from light transmitted through the stack. This image can be of equal or comparable resolution to an image formed from a single fiber faceplate, because little or no light is lost or spread when passing between fiber faceplates in the stack. In some embodiments, the optical filtering layer is configured so that the removable fiber faceplate directly contacts the fixed fiber faceplate, and/or the constituent optical fibers of the removable and fixed fiber faceplates are parallel. An example of such embodiments is shown in FIG. 3, where removable fiber faceplate 304 can be disposed between the fixed fiber faceplate 302 and the transmission filter 305. In some embodiments, the transmission filter of the optical filtering layer is bonded (e.g. coated, camped, mechanically coupled) on the removable fiber faceplate, for example on one side. The removable fiber faceplate can provide mechanical support to the optical filter, and allows easy substitution of optical filters in the contact imaging device.

Figure 4:
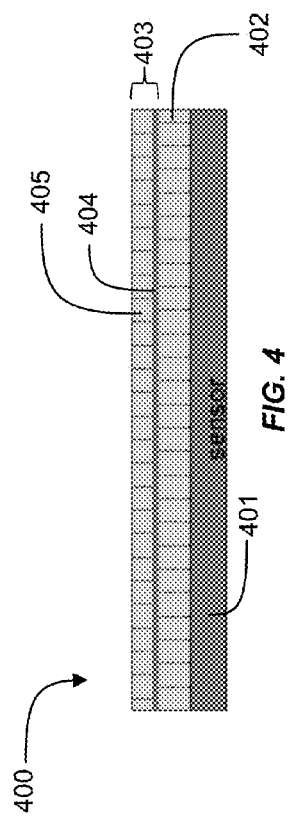
FIG. 4 shows a contact imaging device 400 according to some embodiments of the present invention. Imaging sensor 401 is mechanically coupled to fixed fiber faceplate 402, which is in turn mechanically coupled to optical filtering layer 403. The optical filtering layer includes an interference filter 404 coated on one side of removable fiber faceplate 405. As depicted, the interference filter is disposed between the fixed and removable fiber faceplates. The numerical aperture of the removable fiber faceplate can be lower than that of the fixed fiber faceplate.

The removable fiber faceplate can also be used to ensure that light approaches the transmission filter and/or the imaging sensor at desired angles. For example, in embodiments where the sample array is imaged using fluorescence, excitation light is preferably filtered out. If the transmission filter is an interference filter, such light preferably approaches the transmission filter at a near-zero angle of incidence. The angle of incidence can be reduced by placing the removable fiber faceplate between the excitation light source and the interference filter. Thus, in some embodiments, the transmission filter is disposed between the fixed fiber faceplate and the removable fiber faceplate, as shown in FIG. 4, and/or is in contact with the fixed fiber faceplate. The angle of incidence can be further reduced by using a removable fiber faceplate with a low numerical aperture, or a numerical aperture less than that of the fixed fiber faceplate. In some embodiments, the removable fiber faceplate has a numerical aperture of at most about 0.1, 0.2, 0.3, 0.4, 0.5, 0.6, 0.7, 0.8, 0.9, or 1.0. In some embodiments, the numerical aperture of the removable fiber faceplate is less than that of the fixed fiber faceplate by a difference of at least about 0.01, 0.02, 0.05, 0.1, 0.2, 0.3, 0.4, 0.5, 0.6, 0.7, 0.8, 0.9, 0.95 or 0.99 units. In some embodiments, the fixed fiber faceplate has a numerical aperture of at least about 0.1, 0.2, 0.3, 0.4, 0.5, 0.6, 0.7, 0.8, 0.9, or 1.0.

Generally, fibers in a fiber faceplate as disclosed herein are constructed of an inner fiber made of one optical material and a cladding made of a different material with a different refractive index. Light not perfectly aligned with the axis of the fiber bounces off the interface between the inner fiber and the cladding, staying within the fiber. Accordingly, the angle of acceptance to the fibers in the faceplate can be decreased by replacing some of the fibers in the faceplate with "black" fibers, alternatively referred to as light absorptive fibers. These fibers, either hexagonal or circular, can be spaced in a pattern across the faceplate, and can absorb shallow-angle rays but not interfere with rays perpendicular to the surface of the faceplate.

The fiber faceplates discussed herein, including fixed fiber faceplates and removable fiber faceplates, can include absorptive materials. These materials absorb light of certain wavelengths, and can be the same as or similar to the materials found in the absorptive filters discussed above. For example, absorptive materials include colored glass and black glass. When incorporated into fiber faceplates, absorptive materials can decrease the numerical aperture and/or the angle of acceptance, so that light is selected more stringently on the basis of angle of incidence. In other words, light must approach the faceplate at an angle roughly normal to its surface, or roughly parallel to the long axes of the fibers forming the fiber faceplate, to be transmitted through the faceplate. Absorptive materials can be useful to include in fixed fiber faceplates when the adjacent optical filtering layer includes an absorptive filter. Such filters can be thick and cause blurring in an image of a sample array. A lower numerical aperture in the fixed fiber faceplate that is coupled to the absorptive filter can partially compensate for this blurring. Absorptive materials in the fixed fiber faceplate also permit the omission of a separate absorptive filter in some embodiments.

Figure 5:
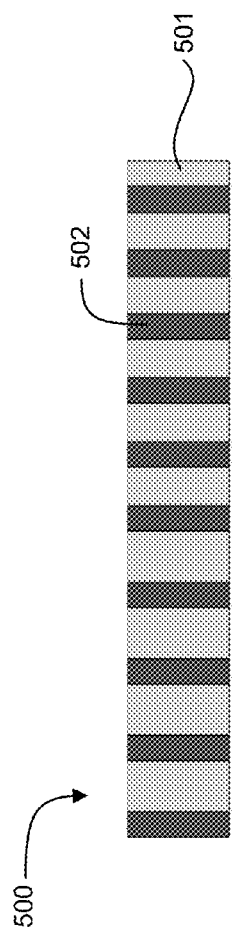
FIG. 5 shows fiber faceplate 500 with fiber optic cores 501 and claddings 502. The claddings include absorptive materials such as colored glass or black glass, according to aspects of the present disclosure.
Figure 6:
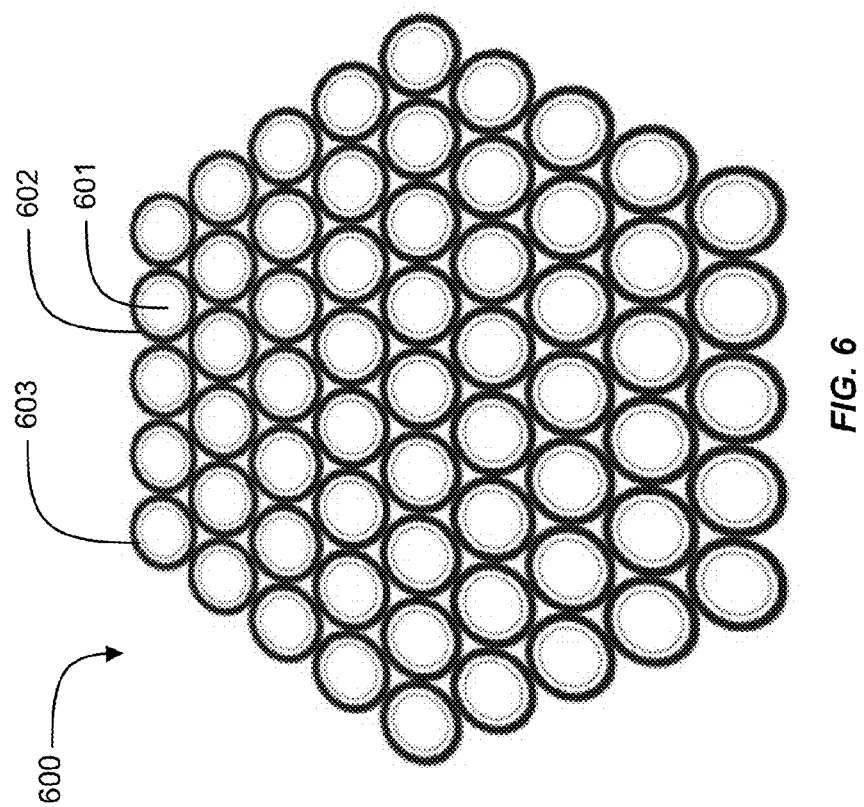
FIG. 6 shows fiber faceplate 600 with fiber optic cores 601 having optical claddings 603 and black claddings 602, according to aspects of the present disclosure.

In some embodiments, the core or cladding of at least one optical fiber in a fiber faceplate includes an absorptive material (FIG. 5). In some embodiments, the core or cladding of all optical fibers in the fiber faceplate is absorptive. Absorptive materials for use in optical fibers can be "black" as defined above. For example, the cladding of one or more optical fibers, or all optical fibers, in a fiber faceplate can be black, as shown in FIG. 6.

Figure 7:
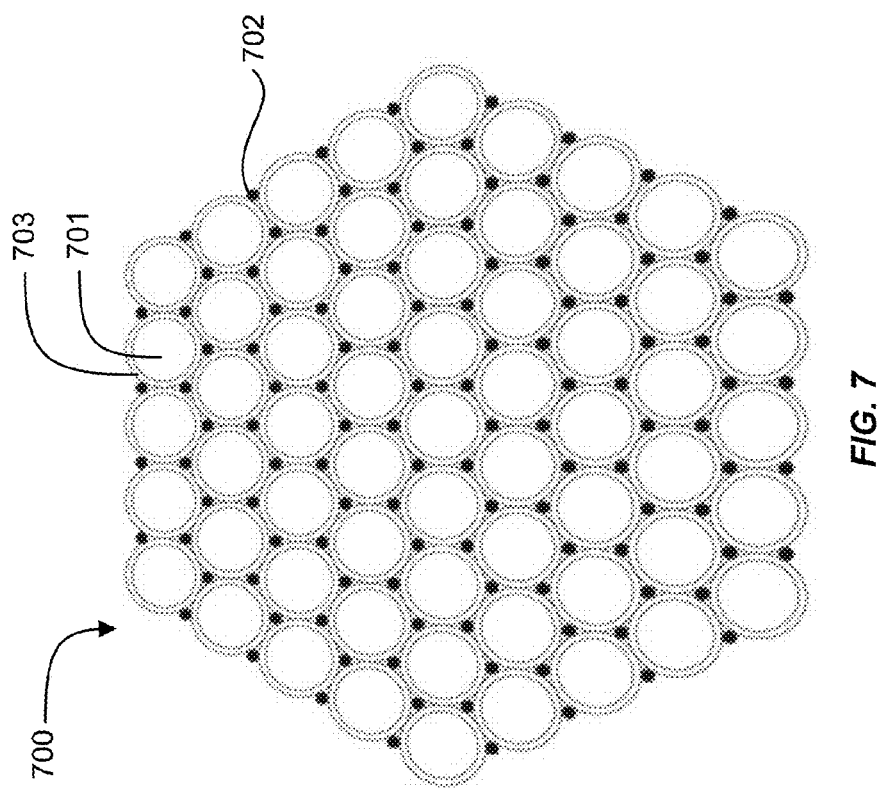
FIG. 7 shows fiber faceplate 700 with black fibers 702 disposed in interstitial spaces between the constituent optical fibers of the faceplate. The optical fibers include cores 701 and claddings 703, according to aspects of the present disclosure.

A fiber faceplate can also include one or more fibers that are fully black, instead of or in addition to fibers with black cladding and light-transmissive cores. A black fiber can have black cladding and a black core, or can be monolithic, i.e., prepared from a single piece of material and/or having a single refractive index. In some embodiments, a fiber faceplate (e.g., the fixed fiber faceplate in the contact imaging device) includes a plurality of black fibers interspersed among a plurality of optical fibers. The black fibers can be disposed in interstitial spaces between optical fibers, as shown in FIG. 7. For ease of manufacturing, or to minimize the angle of acceptance for the fiber faceplate, the black fibers can have circular or hexagonal cross-sections. Any number of black fibers can be included in a fiber faceplate, and these fibers can occupy any useful portion of the faceplate cross-sectional area. In some embodiments, the ratio of the number of black fibers to the number of optical fibers in the fixed fiber faceplate is at most about 1:1,000, 1:500, 1:200, 1:100, 1:50, 1:20, 1:10, 1:5, 1:2, 1:1, 2:1, 5:1, 10:1, 20:1, 50:1, 100:1, 200:1, 500:1, or 1,000:1. In some embodiments, the black fibers occupy at most about 0.1, 0.2, 0.5, 1, 2, 5, 10, 20, 50, 90, 95, or 99 percent of the cross-sectional area of the fixed fiber faceplate. In some of the statistical implementations, the black fiber can occupy up to about 0.6% of the overall area of the fiber faceplate. It will be recognized that when the black fibers in a fiber faceplate are more numerous, or occupy a larger portion of the cross-sectional area, the angle of acceptance and/or numerical aperture of the fiber faceplate can be lowered and the total amount of light transmitted through the fiber faceplate can be reduced.

Figure 8B:
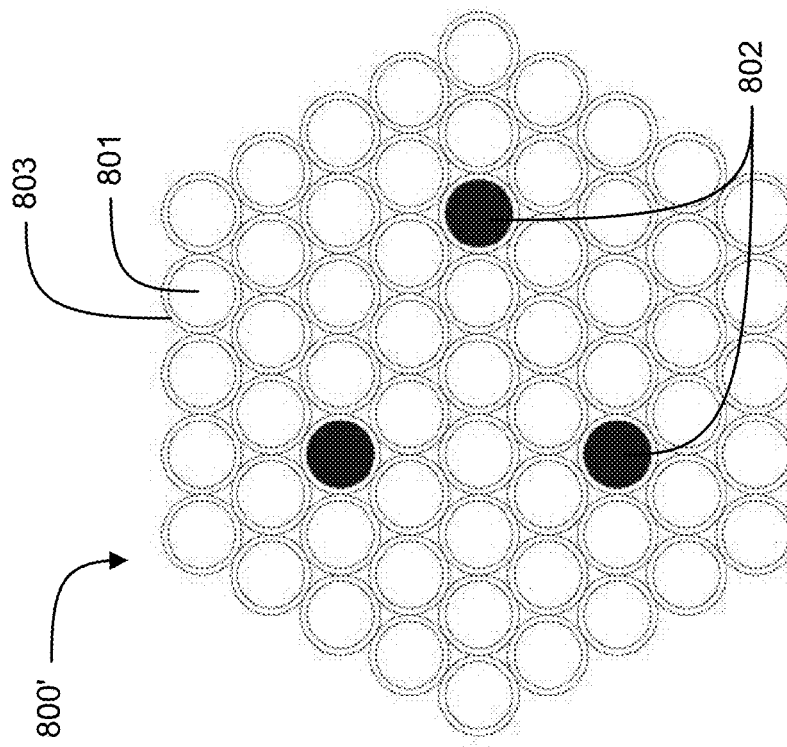
FIG. 8B shows fiber faceplate 800' with fiber optic cores 801 and claddings 803 disposed in combination with black fibers 802, at a ratio of three black fibers 803 per sixty-one total fibers in the fiber faceplate 800', according to aspects of the present disclosure.
Figure 8A:
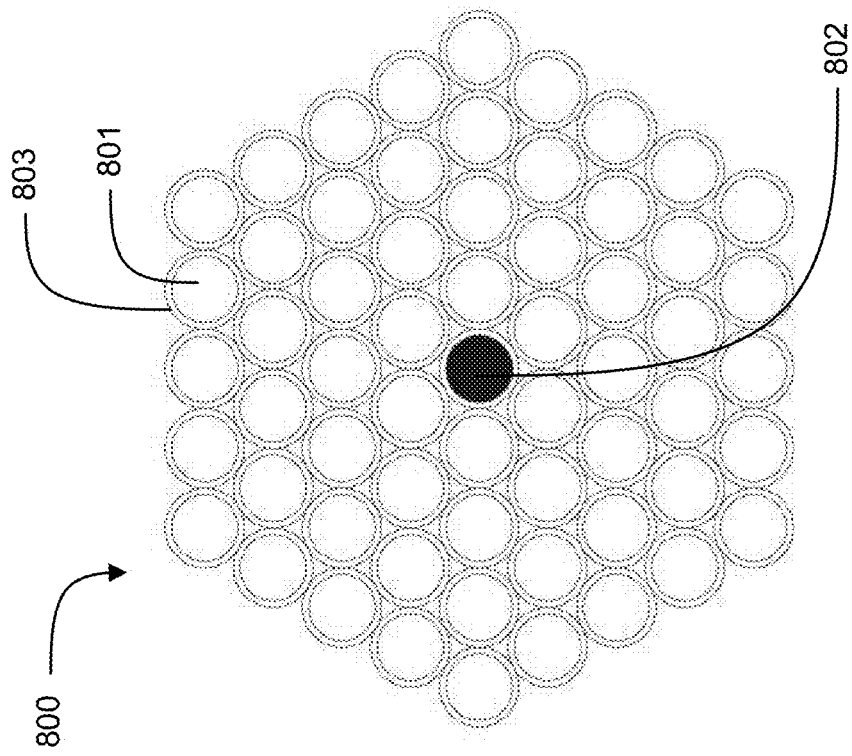
FIG. 8A shows fiber faceplate 800 with fiber optic cores 801 and claddings 803 disposed in combination with black fiber 802, at a ratio of one black fiber 802 per sixty-one total fibers in the fiber faceplate 800, according to aspects of the present disclosure.
Figure 8C:
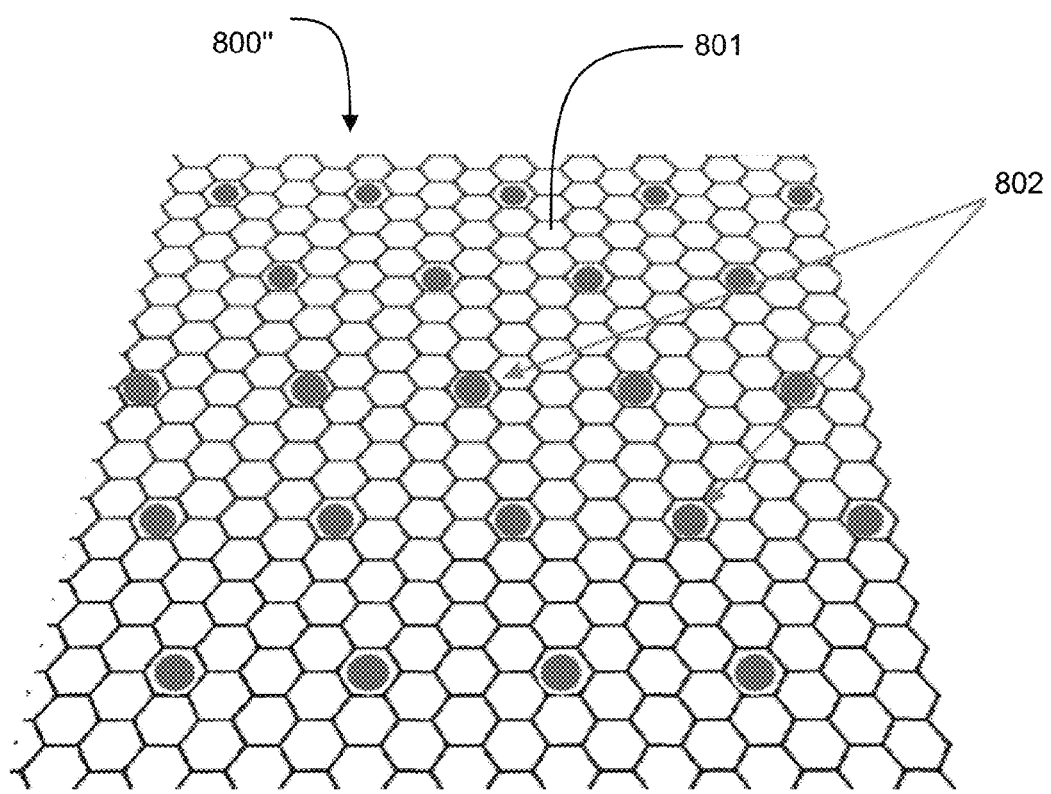
FIG. 8C shows fiber faceplate 800" with fiber optic cores 801 and claddings 803 disposed in combination with black fibers 802, distributed within an array of total fibers for the fiber faceplate 800", according to aspects of the present disclosure.

In further embodiments, a fiber faceplate having one or more fibers that are fully black instead of and replacing fibers with black cladding and light-transmissive cores are shown as in FIG. 8A and FIG. 8B. As shown, a black fiber can have a monolithic black core, where in such embodiments the cladding can be made of the same material as the cladding surrounding the optical fibers of the fiber faceplate. In other aspects, the black fiber cladding can have an absorbance similar to the black fiber, or the black fiber can have a diameter roughly equivalent to the combined diameter of an optical fiber with a cladding. The black fibers can be disposed at various ratios relative to the total number of fibers in the fiber faceplate, such as at one black fiber per sixty-one total fibers as shown in FIG. 8A, or at three black fibers per sixty-one total fibers as shown in FIG. 8B. In further aspects, the number of black fibers in the fiber faceplate can be as few as one black fiber of the total number of fibers in the fiber faceplate, as many as one less than the total number of fibers in the fiber faceplate, or at any increment of fibers within that range. In some of the statistical implementations, the black fiber can occupy about 2%-5% of the overall area of the fiber faceplate. Further, FIG. 8C shows a fiber faceplate with fiber optic cores and claddings disposed in combination with black fibers, evenly distributed within an array of total fibers for the fiber faceplate.

Any of the fiber faceplates discussed above can be provided as a fiber optic taper. Like a fiber faceplate, a fiber optic taper (also called a fiber taper or simply a taper) comprises a bundle of coherent optical fibers, but the fibers have larger diameters at one end than at the other end. As a result, the two surfaces of the fiber optic taper where the optical fibers terminate have unequal areas, with the surface corresponding to the thinner ends of the fibers having a smaller area. Light passing from the smaller surface to the larger surface is magnified, while light passing from the larger surface to the smaller surface is reduced. A fiber optic taper having a magnification ratio (defined as the ratio of the area of the larger surface to the area of the smaller surface) of, for example, at least about 1.1:1, 1.2:1, 1.5:1, 2:1, 5:1, 10:1, 20:1, 50:1, 100:1, 200:1, 500:1, or 1,000:1 can be used in the present devices. In some embodiments of the contact imaging devices, the smaller surface is mechanically coupled to the imaging sensor, which can be smaller than the sensor used with a standard (non-magnifying) fiber faceplate and a sample array of the same size. In other embodiments, the larger surface of the fiber optic taper is mechanically coupled to the imaging sensor to provide clearer images of small sample arrays. As desired, a fiber optic taper can be mechanically coupled to any of the optical filtering layers discussed above, and the fibers making up the fiber optic taper can incorporate absorptive materials.

The presently disclosed devices can include channels embedded in the surface or interior of one or more layers of the device. These channels can accommodate fluids, including a sample and/or analytes of interest. Thus, the sample can be disposed in channels, instead of or addition to a two-dimensional sample array, for imaging. In some embodiments, the channels have microfluidic dimensions. The channels can be disposed in the optical filtering layer, including in an transmission filter and/or removable fiber faceplate. In some embodiments, the channels occur at the interface between two layers of the device (e.g., between the fixed fiber faceplate and optical filtering layer, or between the removable fiber faceplate and transmission filter of the optical filtering layer), or are carved into one surface (e.g., the surface of the optical filtering layer farthest from the imaging sensor). The channels can be coupled to one or more fluid sources, pumps, valves, drains, and other apparatus for fluid handling. It will be recognized that the optics of the contact imaging device can be optimized for imaging samples in channels. For example, a fiber faceplate with an appropriate numerical aperture can be included, or absorptive materials can be placed in one or more layers of the device, so that focused images of channels can be obtained. The present contact imaging devices can be used in conjunction with slideable devices for automated analyte separation and blotting. The slideable devices are disclosed in co-assigned, co-pending U.S. patent application Ser. No. 14/642,487, which is incorporated herein by reference.

Any of the devices disclosed herein can include one or more layers with functionalized surfaces. Such surfaces can facilitate the imaging of samples, for example by allowing the sample to contact the device without denaturation, or allowing layers of the device (e.g., the fixed fiber faceplate and optical filtering layer) to slide past each other with minimal friction. In some embodiments, a surface is functionalized to be hydrophobic or hydrophilic. In some embodiments, a surface is functionalized with a binding partner (e.g., an antibody) for one or more analytes.

E. Imaging Apparatus

Some embodiments of the presently disclosed devices are provided in devices having lids, such as cassettes. A cassette can include an outer shell with a base plate and light-tight lid. Other embodiments of the presently disclosed devices are provided without a lid, as a (outer) shell. The outer shell is made out of a durable material (e.g., plastic, metal, alloy, etc.) and acts to protect the sensor from moisture, dirt, and other contaminants. The outer shell also provides mechanical support to the sensor, fiber faceplate, and/or optical filtering layer, while preventing disruption of image acquisition. The base plate can include a rigid, thermally conductive metal slab (made of, for example, aluminum or an alloy) to which the sensor is thermally bonded or coupled. The slab provides mechanical support to the sensor and reduces temperature gradients across the sensor. The lid can engage the base plate through a clasp, or otherwise close securely to ensure that light does not enter during imaging. In some embodiments, the lid attaches to the base plate using one or more hinges.

The cassette is configured to receive a sample array. In embodiments where the imaging sensor is film, the cassette can also receive a piece of film on the opposite side of the fiber faceplate and optical filtering layer from the sample array. The base plate and lid can act to hold the sample array in place during imaging to avoid blurring of the resulting image. This can be accomplished by ensuring that the lid closes tightly enough over the base plate so that the sample array and film (if present) do not move. The cassette can also include guides, e.g., inside the base plate or on the lid, to hold a sample array of conventional size (such as 5"×7", 8"×10", or 10"×12"). The inside surface of the light-tight lid can include a flexible or semi-rigid material, e.g., rubber or foam padding, or a spring-loaded pad, to allow for some flexibility in the thickness of the sample array. The outer border of the base plate and/or light-tight lid can also include a flexible or semi-rigid material (e.g., a rubber border) to ensure a tight fit.

The base plate holds an imaging sensor as described herein, with a fiber faceplate and optical filtering layer covering the sensor for protection and transmission of signal from the sample array to the sensor. The base plate also is configured to transmit a signal (e.g., data that comprise a digital image) to an external device (e.g., processor, scanner, computer) during or after exposure of the imaging sensor. A control board coupled to the sensor can be used to transmit the signal from the sensor, and communicate it to an external device, optionally with a user interface. The external device can include a touch screen (e.g., integrated in the lid or separate), or be a hand-held device (e.g., tablet or smartphone) or other processor or computer. Communication can occur via cables or ports (e.g., USB or Ethernet) on the cassette, or wirelessly (e.g., using Bluetooth or other wireless transmission).

The presently described devices can be provided in any convenient size. Typical Western blots, dot blots, Northern blots, and Southern blots are on the order of a few inches on either side (e.g., 2×3, 3×4, 4×8 inches), so that a relatively small cassette and sensor detection area will suffice for most assays, e.g., in the range of about 10×12 inches. Sequencing gels are typically larger, thus a cassette having larger dimensions, e.g., in the range of 20×36 inches, can be provided.

In some embodiments, a marker, e.g., an LED (light emitting diode), LCD (liquid crystal display), or small illuminated display, is included in the interior of the cassette or outer shell. The marker can be used to mark an image produced with the imaging sensor, or align a sample array with the imaging sensor. For example, a small LED or back illuminated LCD can be placed in a corner of the lid, baseplate, or fiber plate to mark a designated position on a piece of film serving as the imaging sensor. The LED or LCD can be turned on for a short period so as to avoid saturating the film (e.g., 0.1-2 seconds, depending on the comparative strength of the signal from the sample). In embodiments of the device containing a digital imaging sensor, the strength of the LED or LCD signal can be adjusted, e.g., using a non-destructive readout (NDR) imager. In some embodiments, the LED or LCD is configured into a signature, e.g., user initials, date, etc., and can be replaced or programmed appropriately. For example, the LCD can have back illumination to allow the signal to be shaped into a signature, character, or symbol by programming the crystal device to allow light through in a certain pattern. The LED can comprise a dot array, or be included in an array of LEDs.

F. Assays and Materials

The presently disclosed devices are suited for assays relying on fluorescent, chemiluminescent, bioluminescent, or radioactive signals. Such assays include Western blots, ELISAs, immunoassays, Northern blots (e.g., expression studies using a reporter gene), Southern blots, nucleic acid sequencing assays, and assays involving viral or bacterial labeling (e.g., CFU or expression studies). Assay protocols can be found in, e.g., Walker (2009 $3^{rd}$ ed.) *Protein Protocols Handbook*; Hilario, *Protocols for Nucleic Acid Analysis by Nonradioactive Probes* (2007 $2^{nd}$ ed.); Wenk, A Manual for Biochemistry Protocols (2007); Harris, *Cell Biology Protocols* (2006); etc.

In some embodiments, the assay involves transferring a sample that potentially includes a target analyte (e.g., protein, DNA, or RNA) to a membrane (e.g., blot); and exposing the membrane to a first binding reagent that specifically binds to the target analyte (e.g., labeled probe or antibody). Thus, the membrane can serve as a two-dimensional array for analyte detection. The sample can be on a gel (e.g., electrophoretic gel such as PAGE or agarose gel) or a culture dish before transfer, or can be directly applied to the membrane by the user. As discussed further below, in some embodiments, the assay further involves exposing the membrane to a second binding reagent that specifically binds the first binding reagent (e.g., a labeled secondary antibody, or labeled affinity agent such as streptavidin (to bind biotin on the first binding reagent)). Such assays typically involve washes between binding steps.

In some embodiments, a sample is applied directly to a membrane or other array, e.g., pipetted onto the membrane. This can be useful for controls, e.g., dilution series with known amounts of analyte, or positioning signals.

Once distributed on or in a two-dimensional array, analytes of a sample can be detected as desired, using any convenient technique. In some embodiments, analytes of interest can be detected on the array if they incorporate detectable labels or are linked or conjugated to such labels. Examples of detectable labels include chromophores, fluorophores, and radioactive isotopes. Analytes can also be detected directly, in the absence of labels, if they are optically active. For example, proteins and nucleic acids absorb infrared and ultraviolet radiation and can also exhibit fluorescence. Accordingly, these analytes can be detected by directing light of an appropriate wavelength on the array and measuring an interaction between the light and the analytes. For protein analytes containing tryptophan residues, fluorescence can be enhanced by contacting the analytes with any of several halo-substituted organic compounds, such as chloroform, 2,2,2-trichloroethanol, or 2,2,2-trichloroacetic acid, in the presence of UV radiation. As described in U.S. Pat. Nos. 7,569,130 and 8,007,646 and elsewhere, under such conditions a UV light-induced reaction occurs between the indole moiety of tryptophan and the halo-substituted organic compound, resulting in a fluorescent compound that emits at visible wavelengths.

Detection of analytes can make use of any labels directly or indirectly linked to the analytes, such as those described in U.S. Pat. Nos. 6,165,800, 6,395,503, 6,972,326, and 7,935,489. In some embodiments, the detected labels are fluorescent. Fluorescent dyes that can serve as labels include fluoresceins, rhodamines, coumarins, BODIPYs, and cyanines. Other fluorescent dyes can be used and are reviewed, for example, in Johnson and Spence (Eds.), *Molecular Probes Handbook—A Guide to Fluorescent Probes and Labeling Technologies* (11th ed.), Eugene, Oreg.: 2010. Fluorescent dyes can be conjugated to analytes as desired, using enzymatic addition, Click chemistry, or the Staudinger ligation, among other techniques. In addition to organic dyes, quantum dots ("Q-dots") and fluorescent polymer nanoparticles (polymer dots or "P-dots") can serve as fluorescent labels. Quantum dots having any size, color, or composition can be used, and can be prepared and conjugated to analytes as desired (methods are reviewed, for example, in Medintz et al., *Nature Materials* 4: 435-446, 2005). Similarly, any polymer dots, such as those described in Wu and Chiu, *Angewandte Chemie* 52: 3086-3109, 2013 and elsewhere, can be conjugated to analytes for detection. Fluorescence can also be imparted to analytes by attaching these analytes to fluorescent proteins such as green fluorescent protein (GFP) or yellow fluorescent protein (YFP), which can serve as labels. In recombinant expression systems, a fluorescent protein can be synthesized along with a protein analyte as part of the same polypeptide, such that the fluorescent protein and analyte are covalently tethered together and one renders the other detectable.

In some embodiments, analytes are detected using chemiluminescence. These embodiments involve a chemiluminescent substrate, often a small molecule, that undergoes a chemical reaction and emits light. Some reactions of chemiluminescent substrates can be enzymatically catalyzed. For example, luminol oxidation is catalyzed by peroxidases. The light-emitting decomposition of various phosphorylated 1,2-dioxetanes is catalyzed by phosphatases, and the decomposition of galactose-substituted 1,2-dioxetanes is catalyzed by galactosidase. Tyramide derivatives, as used in tyramide signal amplification techniques, can be converted to tyrosine-reactive free radicals by peroxidases. Other common chemiluminescent substrates and labels include NADP, umbelliferyl phosphate, and p-nitrophenyl phosphate. Enzymes used in chemiluminescence assays include horseradish peroxidase (HRP), alkaline phosphatase, β-D-galactosidase, glucose-6-phosphate dehydrogenase, and xanthine oxidase (see, e.g., Krick (1991) *Clin Chem* 37:1472 for background). Any of these systems, or others known in the art, can be used to detect an analyte of interest by coupling the substrate or the enzyme to the analyte. Thus, either the substrate or the enzyme can serve as a detectable label for the analyte. Upon contacting the substrate with the enzyme, light emission is colocalized with the analyte.

Chemiluminescent systems from living organisms (i.e., bioluminescent systems) can also be harnessed for analyte detection. For example, luciferin can be coupled to an analyte and detected upon exposure to luciferase (e.g., firefly luciferase) or aequorin. Preferably, any coupling of a chemiluminescent substrate, or an enzyme for this substrate, to an analyte for purposes of detection does not interfere with reactions of the substrate. In some embodiments, enzymes used in chemiluminescent detection are coupled to analytes of interest through biotin-avidin linkages. For example, one or more polypeptides of the enzyme can be covalently linked to avidin, and an analyte can be biotinylated. Thus, the enzyme and analyte become linked due to binding between the biotin and avidin moieties.

In other embodiments, detecting the analytes includes contacting the sample array with a binding partner for one or more analytes of the sample, and detecting a signal indicative of binding between the binding partner and the one or more analytes. This kind of detection is used in electroblotting (for example, Southern blotting, northern blotting, and western blotting) and can make use of detection reagents and apparatus used in electroblotting. The binding partner can include an antibody, enzyme, protein (e.g., avidin or streptavidin), peptide, aptamer, ligand, nucleic acid (e.g., nucleotide or oligonucleotide), nucleic acid analog, coordination complex, natural or synthetic polymer, carbohydrate, or small molecule (e.g., biotin). In particular, when analytes of the sample are proteins, the binding partner can be an antibody. This antibody can be directed to an epitope in one or more analytes of interest. The antibody can be detectable directly, for example by bearing a fluorescent label, or can be detectable using a secondary antibody and/or chemiluminescence. When analytes of interest are nucleic acids, the binding partner(s) can be complementary nucleic acid sequences bearing fluorescent or radioactive labels. Other probes for various types of analytes are known, and many types of signal indicative of binding can be detected. In some embodiments, the signal includes chemiluminescence, electroluminescence, fluorescence, infrared radiation, radioactivity, color, or optical absorbance. In general, the analytes and binding partner can be part of a biosensor system, which can employ additional molecular components or detection apparatus.

The signal arising from the binding between an analyte and its binding partner can be amplified using any convenient technique. For example, when an analyte is detected using one or more antibodies, the signal can be amplified using tyramide radicals. The signal can also be amplified using a proximity ligation assay, in which two different oligonucleotide-linked antibodies colocalize, so that the oligonucleotides can be ligated together and amplified. Instead or in addition, one or more detectable labels, such as fluorophores, polymer dots, or quantum dots, can be conjugated to the analyte and/or binding partner to supplement signals such as those discussed above. Conjugation can employ biotin-avidin interactions, for example. If a fluorophore is coupled to each of the analyte and binding partner, and the two fluorophores have overlapping excitation and emission spectra, then binding can be detected using fluorescence quenching or fluorescence resonance energy transfer (FRET). In some embodiments, additives such as crowding agents (e.g., polyethylene glycol or dextrans) are contacted with the sample array during detection to increase the rates of binding between an analyte and its binding partner.

If desired, two or more binding partners can be used, simultaneously or at different times, to detect analytes on the same sample array. The binding partners can be specific for the same analyte, different forms (e.g., phosphorylated and unphosphorylated) of the same analyte, or different analytes entirely. These binding partners can give rise to the same signal, measurably different signals (for example, fluorescence of different emission wavelengths), or orthogonal types of signals (for example, fluorescence and radioactivity). Using multiple binding partners can provide more informative analyte detection than is possible with a single binding partner. For example, two binding partners can reveal the relative amounts of two different analytes immobilized on the array or the relative positions of the analytes on the array. Alternatively, two different antibodies directed to the same analyte can probe for the presence, integrity, or accessibility of two different epitopes.

Detecting analytes on the sample array can require, in some embodiments, exposing the binding partner for the analytes to a reagent. The reagent can bind to or react with the binding partner in order to generate a detectable signal. For example, if the analytes are proteins and the binding partner is an antibody, the reagent can be a chemiluminescent substrate (e.g., luminol) that can be oxidized by an enzymatic domain (e.g., horseradish peroxidase) coupled to the antibody. The substrate can be added to a solution in which the array is submerged, and does not become coupled to the analytes or antibody, but the chemiluminescent signal reveals the location of antibody-bound analytes. In order to amplify the light emitted by oxidation of the substrate and achieve enhanced chemiluminescence, a chemical such as p-iodophenol can also be added. When an antibody serves as binding partner to the analytes, the reagent used for purposes of detection can alternatively be a labeled secondary antibody. It will be recognized that detection can make use of multiple reagents in addition to the binding partner.

In some cases, detecting analytes on the array can involve applying a blocking agent. The blocking agent can bind non-specifically to the array, for example in locations where analytes are not immobilized, and prevent binding partners for the analytes from also binding non-specifically in these locations. The blocking agent can thus reduce background signal and allow more precise detection of analytes. Examples of blocking agents include proteins such as bovine serum albumin or milk proteins. Preferably, the blocking agent is applied to the array before the array is contacted with binding partners.

If desired, an array carrying a sample (e.g., a membrane to which proteins, nucleic acids, or other analytes have been transferred) can be exposed to an index-matching fluid. The index matching fluid increases the transparency of the array, and/or matches the refractive index of the fiber faceplate or sensor in the device. Thus, the index-matching fluid prevents the array itself from perturbing optical signals arising from analytes in the array. For example, the fluid can reduce reflections at the interface between the array and fiber faceplate. Examples of index matching fluids are fused silica matching fluids from Cargille.

In some embodiments, assays involve a radioisotope label, e.g., radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Ln, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga.

G. Systems

A system according to embodiments of the present invention includes a contact imaging device as described above, and a light source (e.g., an excitation light source). The light source can be used to illuminate a sample or sample array placed in contact with the device for imaging. Examples of light sources include incandescent bulbs, fluorescent bulbs, light-emitting diodes (LEDs), and lasers. In some embodiments, the light source emits across a wide range of wavelengths (e.g., about 50, 100, 200, 300, 400, or 500 nm), while in other embodiments emissions are confined to narrow wavelength bands (e.g., about 5, 10, 20, 50, 100, or 200 nm) or single wavelengths. If desired, the light source can be collimated. Light sources emitting in the ultraviolet, visible, and/or infrared portions of the electromagnetic spectrum can all be used in the present systems. The light source can be chosen as appropriate for one or more of the assays described above. For example, the light source can emit wavelengths of light to excite fluorescent labels on analytes of interest.

The system can further include a fluorescent, phosphorescent, or chemiluminescent sample. The sample can include one or more species or analytes that can be detected optically. The sample can be disposed in a two-dimensional sample array such as an electrophoresis gel or blotting membrane, as discussed above, which can be placed in proximity to the contact imaging device. Alternatively, the sample can be applied directly to the contact imaging device, such as to an exposed surface of the optical filtering layer. Embodiments of the system can be configured such that light emitted by the excitation light source passes through the sample. For example, excitation light can travel perpendicular to the plane of a two-dimensional sample array, or at a small angle to this plane, and pass through the sample array before reaching the contact imaging device.

In some embodiments, the system includes an excitation fiber faceplate, which is configured to be disposed between the excitation light source and the sample. The excitation fiber faceplate can share characteristics with any of the fiber faceplates discussed above (for example, fixed fiber faceplates, removable fiber faceplates, or fiber optic tapers), and guides light from the light source to the sample. The excitation fiber faceplate can thus be used to control the geometry of light rays reaching the sample and imaging sensor. Any distance can be established between the light source and excitation fiber faceplate, and if desired the excitation fiber faceplate can be mechanically coupled to the light source.

Figure 9C:
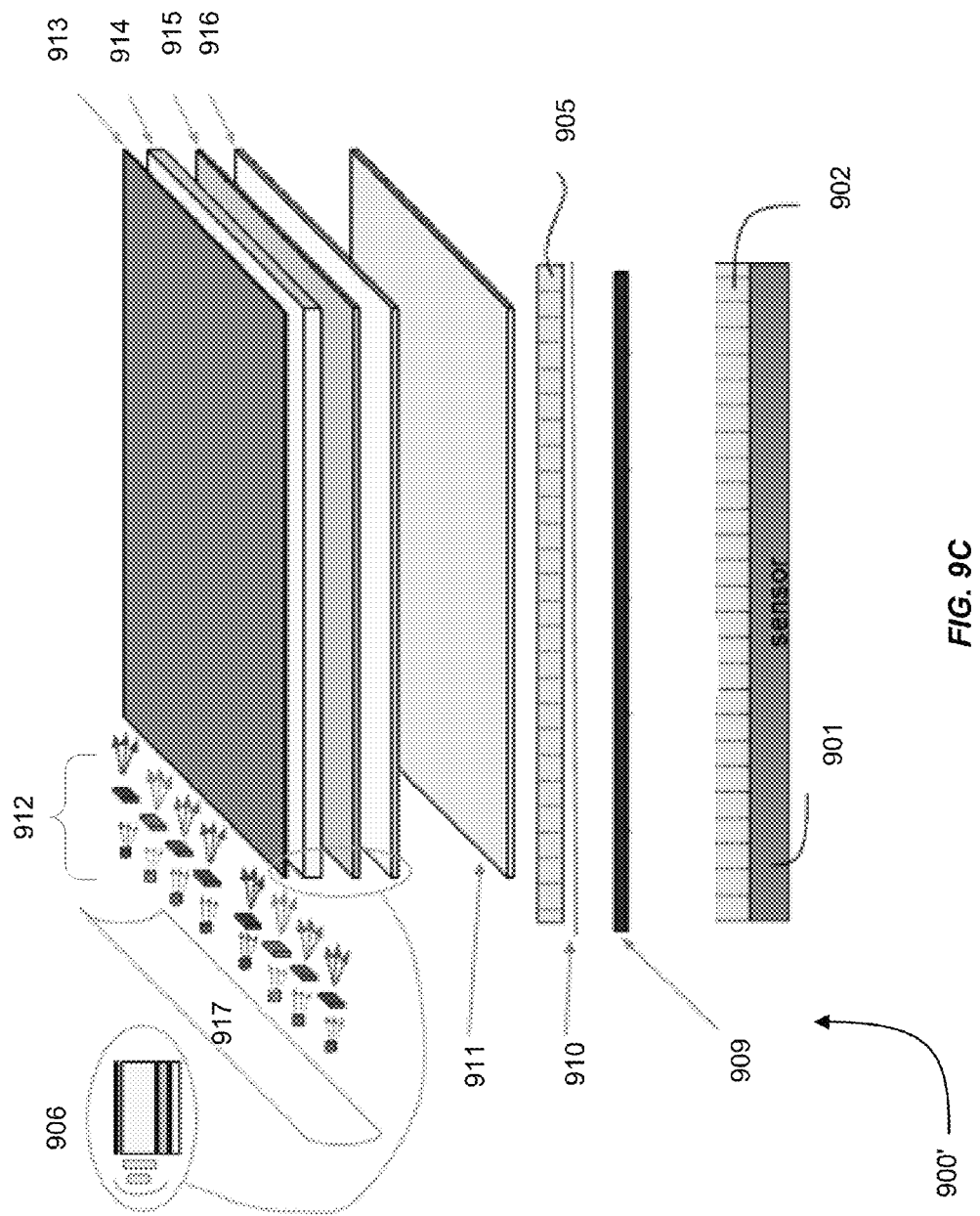
FIG. 9C shows an exploded view of the system 900' shown in FIG. 9B, further illustrating a lighting source according to some embodiments of the present invention. The light source 906 is positioned on one side of the sample gel 911 such that light transmits through the sample gel 911 toward and through the excitation fiber faceplate 905, absorbance glass 909, and fixed fiber faceplate 902 to the sensor 901. The light source 906 can be referred to as a total internal reflection (TIR) structure, including an LED structure 912 having one or more color LEDs as the primary source of illumination. In some aspects, the LED structure 912 can have one or more sets of color or white light LEDs. In further aspects, the LEDs can have filters placed between each LED and a clear TIR layer 914. The TIR structure can include (in order further from the sample gel 911 to closest) a reflective layer 913, the clear TIR layer 914, a diffuser 915, and a secondary clear layer 916. The LEDs 912 can be positioned to illuminate on the side of the clear TIR layer 914, with the light transmitting through the clear TIR layer 914. The reflective layer 913 directs light incident upon it back toward the sample gel 911. The diffuser 915 can even out the light as it transmits toward the sample gel 911. The secondary clear layer 916 can provide a physical limit to the TIR structure while passing the light from the light source to the sample gel 911. A side reflector 917 can be positioned on a side of the LED structure 912 opposite of the TIR structure to redirect light back toward the TIR structure. In further embodiments, the light source 906 can be located on one side of the TIR structure, two sides of the TIR structure, three sides of the TIR structure, or on all sides of the TIR structure.

In some embodiments, the excitation fiber faceplate has a low numerical aperture, and only transmits light that is approximately normal to the surface of the faceplate. The numerical aperture can be at most about 0.05, 0.1, 0.2, 0.3, 0.4, 0.5, 0.6, 0.7, 0.8, 0.9, or 1.0, for example. If the excitation fiber faceplate is roughly parallel to the optical filtering layer of the contact imaging device, then light arrives at the sample plane and optical filtering layer at a low angle of incidence (FIGS. 9A & 9B). Accordingly, the optical filtering layer can be engineered, such as by incorporating an interference filter, to prevent excitation light from passing through and reaching the imaging sensor. In some embodiments, light emitted by the light source and transmitted by the excitation fiber faceplate is collimated, because the light source itself is collimated, and/or because the excitation fiber faceplate passes only light rays having small angles of incidence. In further embodiments (FIG. 9C) a TIR structure can be used to emit evenly diffused light toward the sample and fiber faceplate.

Figure 10:
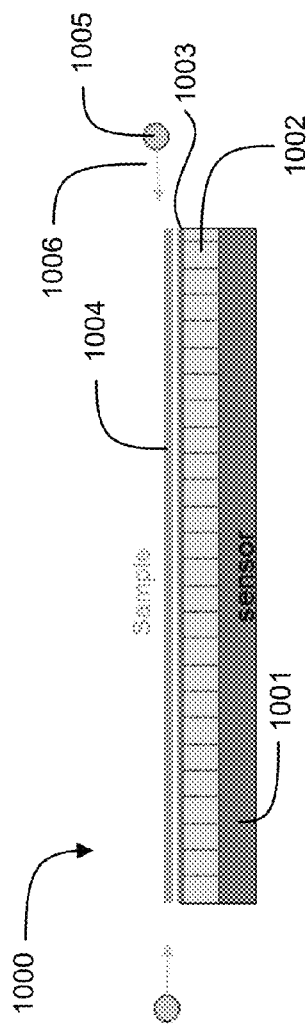
FIG. 10 shows a system 1000 for imaging a fluorescent sample according to some embodiments of the present invention. A contact imaging device includes imaging sensor 1001, fixed fiber faceplate 1002, and optical filtering layer 1003. Optical filtering layer 1003 includes an optical filter, such as an interference filter or an absorptive filter. Two-dimensional sample array 1004 is placed in contact with optical filtering layer 1003 and lies roughly flat. Light source 1005 is positioned to the side of the contact imaging device, such that light rays 1006 travel nearly parallel to the surface of the optical filtering layer, and strike sample array 1004 at a high angle of incidence. In some cases, these rays pass through the sample array before exciting analytes of interest.

As an alternative to the light source being placed directly above the contact imaging device (e.g., with light rays arriving at the optical filtering layer at an angle perpendicular to its surface), the light source can be placed to the side of the contact imaging device (FIG. 10). Thus, light enters the sample array from the side, and most or all light striking the optical filtering layer results from reflections or fluorescent emissions from analytes in the sample array. In this configuration, the geometry of the system prevents excitation light from reaching the imaging sensor. In some embodiments, the excitation light source is positioned relative to the contact imaging device such that light emitted by the excitation light source is not incident on the optical filtering layer. For example, the excitation light source can be placed beside and below the sample plane of the contact imaging device, so no light rays from the light source directly fall on the optical filtering layer. In some embodiments, the excitation light source is positioned relative to the contact imaging device such that light emitted by the excitation light source is incident on the optical filtering layer at an angle of at least about 1, 2, 3, 4, 5, 6, 7, 8, 9, 10, 20, 30, 40, 50, 60, 70, 80, or 90 degrees from the normal. In these embodiments, the optical filtering layer can incorporate an absorptive filter to remove excitation light approaching at high angles of incidence. The light source can also be positioned so that excitation light travels in a direction parallel to the surface of the optical filtering layer. For example, the excitation light source can be a laser, with the beam directed across the surface or from the side of the optical filtering layer but not striking the surface. In further embodiments, the optical filtering layer can be backlit, with a reflective material, a light source, or through a light filter (FIG. 9C).

H. Methods

The devices and systems disclosed above can be used to carry out contact imaging of fluorescent, phosphorescent, or chemiluminescent samples. In the present methods, a sample is placed in proximity to the contact imaging device. For example, a two-dimensional sample array is placed on the optical filtering layer of the device, or the sample is otherwise applied to this layer as desired. The sample is then exposed to an excitation light source, and an image of the sample is obtained using the imaging sensor of the contact imaging device.

Any of the excitation light sources discussed above (for example, an LED or a laser) can be used in the present methods. The light source can be positioned above the sample, to the side of the sample, or elsewhere, and can be actuated as desired. Likewise, the imaging sensor can be actuated as desired, for example using an external control board in the case of a CCD or CMOS sensor. In some embodiments, the light source and imaging sensor are under the control of common circuitry or software to properly time exposure and image acquisition, and/or ensure that an appropriate amount of light is used to form the image. The ambient light level around the contact imaging device can be set as desired, for example by placing the device in a dark room or enclosing the device in a light-tight cassette (discussed above).

In some embodiments, an image of the sample is obtained at the same time the sample is exposed to an excitation light source. This can be done when fluorescent analytes are being detected, and the image is formed from light fluorescently re-emitted from the analytes upon excitation. Simultaneous imaging and exposure to excitation light can be necessary when the fluorescence lifetimes of analytes in the sample are short, on the order of milliseconds or less. Such lifetimes make it impractical to acquire an image after the light source has been turned off. In these embodiments, the fixed fiber faceplate and optical filtering layer of the contact imaging device can be engineered as described above to prevent excitation light from reaching the imaging sensor. Similarly, the excitation light source can be positioned or otherwise configured (for example, placed behind an excitation fiber faceplate) to minimize exposure of the imaging sensor to excitation light.

In other embodiments, the image of the sample is obtained using time-resolved fluorescence techniques. For example, the image can be acquired using fluorophores with long-lived excited states; pulsed lasers with optical gating; fast-detection electronics; and/or an imaging sensor with nanosecond or picosecond time resolution. In these embodiments, an image can be formed from light fluorescently emitted from the sample after the excitation light source has been turned off. The method can be performed similarly for phosphorescent samples, which can emit light for many seconds or minutes after exposure to excitation light. It will be recognized that the ability to expose and image a sample in sequential steps, such that imaging occurs with the excitation light source turned off, affords greater flexibility in the configuration of the present devices and systems. For example, the fixed fiber faceplate and optical filtering layer do not need to be designed to block excitation light, and the excitation light source can be positioned where most convenient, rather than in a place where it is not incident on the imaging sensor.

Figure 11:
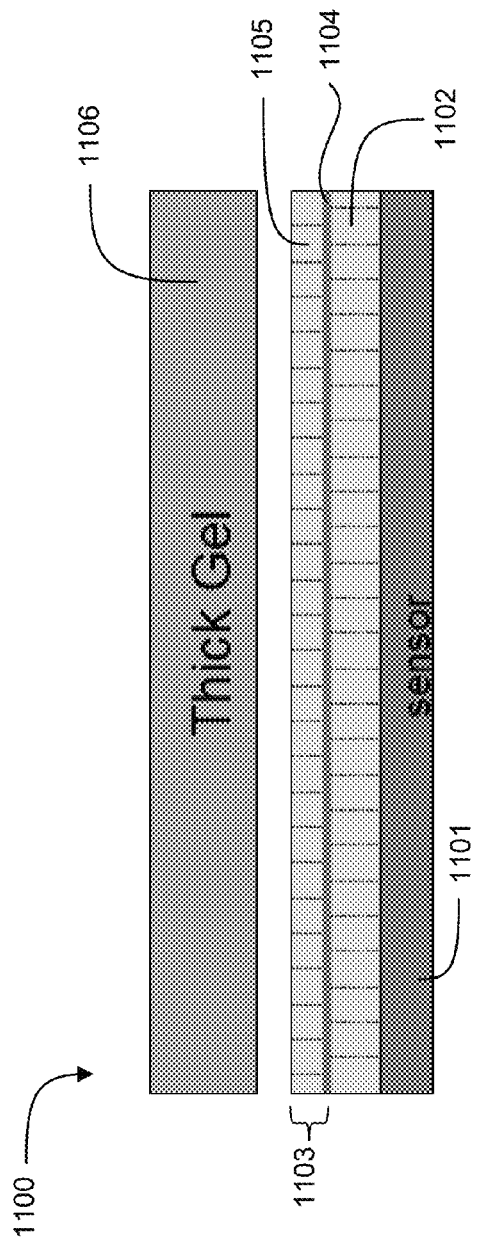
FIG. 11 shows a contact imaging device 1100 according to some embodiments of the present invention. Imaging sensor 1101 is mechanically coupled to fixed fiber faceplate 1102, which is turn mechanically coupled to optical filtering layer 1103. The optical filtering layer includes interference filter 1104 coated on one side of removable fiber faceplate 1105. The interference filter is disposed between the fixed and removable fiber faceplates. Thick sample array 1106 contacts removable fiber faceplate 1105 and can be exposed to an excitation light source (not shown). Removable fiber faceplate has a low numerical aperture, and provides a high depth of field for imaging analytes in sample array 1106.

The present methods can also apply image-sharpening algorithms to images obtained using the contact imaging devices. These algorithms can compensate, in whole or in part, for reduced spatial resolution in the images, which can result from a poor source image from the faceplate, an image received from a misplaced or non-ideal location on a sensor, a miscalibrated sample or sensor, or blurring. Blurring can in turn result from the light emitted by analytes of interest passing through a thick sample array (FIG. 11), optical filter, or other non-light-guiding material to reach the imaging sensor. Standard image-sharpening algorithms can be used, such as deconvolution with an Airy disc point-spread function.

I. Kits

Embodiments of the present invention are also provided as kits for imaging fluorescent, chemiluminescent, or phosphorescent samples in a contact imaging configuration. A kit includes an imaging sensor mechanically coupled to a fixed fiber faceplate, as discussed above under "Devices." The kit also includes two or more optical filtering layers (e.g., a first optical filtering layer and a second optical filtering layer) that can be substituted for each other in a contact imaging device. Each optical filtering layer includes a removable fiber faceplate and an optical filter, the removable fiber faceplate being bonded (e.g. coated, camped, mechanically coupled) on one side with the optical filter, and is configured to be mechanically coupled to the fixed fiber faceplate. The optical filtering layers can be swapped in and out of the contact imaging device as desired to image different samples, or image the same sample in different configurations.

In some embodiments, the optical filtering layers in a kit are distinguished from each other by the ranges of wavelengths that they pass or filter out. For example, one optical filtering layer can include a short-pass optical filter, while another includes a long-pass optical filter. The optical filtering layers can also pass light in different wavelength bands. For example, using band-pass optical filters, a first optical filtering layer can pass long-wavelength visible light (e.g., red light), and a second optical filtering layer can pass short-wavelength visible light (e.g., blue light). Both such optical filtering layers can block medium-wavelength visible light (e.g., green light), infrared light, and/or ultraviolet light. In these embodiments, the choice of an optical filtering layer for a particular assay can be based on the wavelengths of light emitted by analytes in the sample, or the wavelengths of light used to excite the analytes.

The optical filtering layers in a kit can be distinguished by additional characteristics of the transmission filter and/or removable fiber faceplate in each layer. In some embodiments, the transmission filter of a first optical filtering layer is a dielectric filter, and the transmission filter of a second optical filtering layer is an absorptive filter. As discussed above, dielectric and absorptive filters differ in the efficiency with which they filter light at different angles of incidence. Similarly, removable fiber faceplates admit light at different incident angles depending on the numerical aperture. In some embodiments, the removable fiber faceplates of first and second optical filtering layers have different numerical apertures. By including optical filtering layers that efficiently filter or pass light in different ranges of angles, a kit can be used with different kinds of sample arrays (e.g., thick or thin) and different configurations of the light source (e.g., above the sample array or to the side).

The optical filtering layers in a kit can also be distinguished by the intended orientation of the removable fiber faceplate and transmission filter with respect to the fixed fiber faceplate. In some embodiments, a first optical filtering layer is configured for the removable fiber faceplate to be disposed between the fixed fiber faceplate and the optical filter, and a second optical filtering layer is configured for the transmission filter to be disposed between the fixed fiber faceplate and the removable fiber faceplate. In other words, an optical filtering layer can be configured for either the removable fiber faceplate or the transmission filter to be disposed adjacent to the fixed fiber faceplate, and a kit can include optical filtering layers optimized for both such configurations.

As discussed above, placing the removable fiber faceplate in contact with the fixed fiber faceplate allows light to be guided through both faceplates without loss, for example from the transmission filter to the imaging sensor. This configuration can provide increased mechanical support for the contact imaging device and/or the sample. Alternatively, placing the transmission filter in contact with the fixed fiber faceplate, such that the removable fiber faceplate faces the sample, allows light from the sample to be filtered first on the basis of incident angle before it is filtered on the basis of wavelength. With either orientation, the removable fiber faceplate and transmission filter of an optical filtering layer can be chosen in concert to pass light of appropriate wavelengths and incident angles for the imaging task at hand. In some embodiments, one or more optical filtering layers in a kit are reversible, in that either side of the optical filter layer (presenting the removable fiber faceplate or the optical filter) can be mechanically coupled to the fixed fiber faceplate.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. For example, any of the aspects described above may be combined into one or several different configurations, each having a subset of aspects. Further, throughout the foregoing description, for the purposes of explanation, numerous specific details were set forth in order to provide a thorough understanding of the invention. The specific embodiments described herein are offered by way of example only and are not meant to be limiting in any way. It is intended that the specification and examples be considered as exemplary only, with the true scope and spirit of the invention being indicated by the following claims.

What is claimed is:

1. A contact imaging device comprising:
   an imaging sensor;
   a fixed fiber faceplate directly mechanically coupled to the imaging sensor, wherein the fixed fiber faceplate comprises a plurality of optical fibers and an absorptive material, wherein the absorptive material of the fixed fiber faceplate comprises a plurality of black fibers interspersed among the plurality of optical fibers, disposed in interstitial spaces between the optical fibers; and
   an optical filtering layer mechanically coupled to the fixed fiber faceplate, wherein the optical filtering layer further comprises a removable fiber faceplate and a transmission filter, wherein the transmission filter is an interference filter or an absorptive filter, wherein the removable fiber faceplate is bonded on one side with the transmission filter, and wherein the optical filtering layer is configured to be removed from the fixed fiber faceplate.

2. The contact imaging device of claim 1, wherein the optical filtering layer comprises an interference filter, wherein the interference filter is configured to be a long-pass filter, to block ultraviolet light, or to pass visible light, or a combination thereof.

3. The contact imaging device of claim 2, wherein the optical filtering layer comprises an absorptive filter, and wherein the absorptive filter is disposed between the interference filter and the fixed fiber faceplate.

4. The contact imaging device of claim 1, wherein the absorptive material further comprises the core or the cladding of at least one of the optical fibers.

5. The contact imaging device of claim 1, wherein the numerical aperture of the removable fiber faceplate is less than that of the fixed fiber faceplate.

6. The contact imaging device of claim 1, wherein the removable fiber faceplate is disposed between the fixed fiber faceplate and the transmission filter, or wherein the transmission filter is disposed between the fixed fiber faceplate and the removable fiber faceplate.

7. The contact imaging device of claim 1, wherein the fixed fiber faceplate is a fiber optic taper.

8. The contact imaging device of claim 1, wherein the angle of acceptance of optical fibers of the fixed fiber faceplate is at most about 30 degrees.

9. The contact imaging device of claim 1, wherein the black fibers have circular or hexagonal cross-sections.

10. The contact imaging device of claim 1, wherein the plurality of black fibers are at a ratio of the number of black fibers to the number of optical fibers from 1:61 to 60:61.

11. The contact imaging device of claim 1, wherein the plurality of black fibers occupy about 10 percent of the cross-sectional area of the fixed fiber faceplate.

12. A system for imaging a fluorescent, phosphorescent, or chemiluminescent sample, the system comprising:
    an excitation light source; and
    a contact imaging device, the contact imaging device comprising:
        an imaging sensor;
        a fixed fiber faceplate mechanically coupled to the imaging sensor, wherein the fixed fiber faceplate comprises a plurality of optical fibers and a plurality of absorptive material fibers disposed in interstitial spaces between the plurality of optical fibers;
        an optical filtering layer mechanically coupled to the fixed fiber faceplate; and
        an excitation fiber faceplate, wherein the excitation fiber faceplate is disposed between the excitation light source and the sample.

13. The system of claim 12, further comprising a cassette, wherein the cassette comprises a base plate and a light-tight lid, and the contact imaging device is mechanically coupled to the base plate, wherein the base plate comprises a thermally conductive metal slab, and the imaging sensor is coupled to the metal slab.

14. The system of claim 12, wherein light emitted by the excitation light source and transmitted by the excitation fiber faceplate is collimated.

15. The system of claim 12, wherein the excitation light source is positioned relative to the contact imaging device such that light emitted by the excitation light source is not incident on the optical filtering layer.

16. The system of claim 12, wherein the excitation light source is positioned relative to the contact imaging device such that light emitted by the excitation light source is incident on the optical filtering layer at an angle of at least about 30 degrees from the normal.

17. The system of claim 12, wherein the excitation light source is positioned relative to the contact imaging device such that the excitation light source emits light in a direction parallel to the surface of the optical filtering layer.

18. The system of claim 12, wherein the system is adapted to run one any one or a combination of a Western blot, a dot blot, a Northern blot, or a Southern blot.

19. The system of claim 12, wherein the surface of the excitation fiber faceplate arranged to face the excitation light source has a numerical aperture of at most 1.0.

20. The system of claim 12, wherein the absorptive material fibers have circular or hexagonal cross-sections.

21. The system of claim 12, wherein the plurality of absorptive material fibers are present at a ratio of the number of absorptive material fibers to the number of optical fibers from 1:61 to 60:61.

22. The system of claim 12, wherein the plurality of absorptive material fibers occupy about 10 percent of the cross-sectional area of the fixed fiber faceplate.

* * * * *